United States Patent
Kanatzidis et al.

(10) Patent No.: US 9,803,136 B2
(45) Date of Patent: Oct. 31, 2017

(54) LIQUID ELECTROLYTE-FREE, SOLID-STATE SOLAR CELLS WITH INORGANIC HOLE TRANSPORT MATERIALS

(71) Applicant: Northwestern University, Evanston, IL (US)

(72) Inventors: Mercouri G. Kanatzidis, Wilmette, IL (US); In Chung, Evanston, IL (US); Byunghong Lee, Evanston, IL (US); Robert P. H. Chang, Glenview, IL (US)

(73) Assignee: Northwestern University, Evanston, IL (US)

( * ) Notice: Subject to any disclaimer, the term of this patent is extended or adjusted under 35 U.S.C. 154(b) by 932 days.

(21) Appl. No.: 13/772,794

(22) Filed: Feb. 21, 2013

(65) Prior Publication Data

US 2013/0233377 A1    Sep. 12, 2013

Related U.S. Application Data

(60) Provisional application No. 61/601,262, filed on Feb. 21, 2012, provisional application No. 61/601,219, filed on Feb. 21, 2012.

(51) Int. Cl.
*H01L 31/044* (2014.01)
*C09K 11/66* (2006.01)
(Continued)

(52) U.S. Cl.
CPC ............ *C09K 11/665* (2013.01); *C09K 11/06* (2013.01); *F21K 2/00* (2013.01); *F21V 9/04* (2013.01);
(Continued)

(58) Field of Classification Search
CPC ........ H01L 31/00–31/078; Y02E 10/50–10/60
(Continued)

(56) References Cited

U.S. PATENT DOCUMENTS 3,580,748 A    5/1971    DeLong
5,882,548 A    3/1999    Liang et al.
(Continued)

FOREIGN PATENT DOCUMENTS

EP    1176618    1/2002
EP    2280404    2/2011
(Continued)

OTHER PUBLICATIONS

Akihiro Kojima, Kenjiro Teshima, Yasuo Shirai, Tsutomu Miyasaka, Organometal Halide Perovskites as Visible-Light Sensitizers for Photovoltaic Cells, Journal of the American Chemical Society Communication, 2009.*

(Continued)

*Primary Examiner* — Bach Dinh
(74) *Attorney, Agent, or Firm* — Bell & Manning, LLC

(57) ABSTRACT

Photovoltaic cells incorporating the compounds A/M/X compounds as hole transport materials are provide. The A/M/X compounds comprise one or more A moieties, one or more M atoms and one or more X atoms. The A moieties are selected from organic cations and elements from Group 1 of the periodic table, the M atoms are selected from elements from at least one of Groups 3, 4, 5, 13, 14 or 15 of the periodic table, and the X atoms are selected from elements from Group 17 of the periodic table.

34 Claims, 31 Drawing Sheets

(51) Int. Cl.
| | | |
|---|---|---|
| H01L 31/032 | (2006.01) | |
| H01G 9/20 | (2006.01) | |
| C09K 11/06 | (2006.01) | |
| F21K 2/00 | (2006.01) | |
| F21V 9/04 | (2006.01) | |
| F21V 9/16 | (2006.01) | |
| G01N 21/64 | (2006.01) | |

(52) U.S. Cl.
CPC ........... *F21V 9/16* (2013.01); *G01N 21/6402* (2013.01); *H01G 9/20* (2013.01); *H01L 31/032* (2013.01); *C09K 2211/10* (2013.01); *H01G 9/2059* (2013.01); *Y02E 10/542* (2013.01)

(58) Field of Classification Search
USPC .................................................. 136/243–265
See application file for complete search history.

(56) References Cited

U.S. PATENT DOCUMENTS

| | | | |
|---|---|---|---|
| 6,880,746 | B2 | 4/2005 | Seseke-Koyro et al. |
| 8,529,797 | B2 † | 9/2013 | Shum |
| 2002/0036298 | A1 | 3/2002 | Nelles et al. |
| 2002/0153510 | A1 | 10/2002 | Sun et al. |
| 2005/0109385 | A1 | 5/2005 | Kim et al. |
| 2007/0085051 | A1 | 4/2007 | Sohn et al. |
| 2008/0014463 | A1 | 1/2008 | Varadarajan et al. |
| 2008/0038494 | A1 | 2/2008 | Midgley et al. |
| 2008/0202583 | A1 | 8/2008 | Lee |
| 2009/0095341 | A1 | 4/2009 | Pfenninger et al. |
| 2009/0126784 | A1 | 5/2009 | Pak et al. |
| 2009/0211638 | A1* | 8/2009 | Park .................... H01G 9/2072 136/262 |
| 2010/0032018 | A1 † | 2/2010 | Zhu |
| 2010/0051101 | A1* | 3/2010 | Kim ...................... B82Y 10/00 136/256 |
| 2010/0055350 | A1 | 3/2010 | Pfenninger et al. |
| 2010/0316331 | A1 | 12/2010 | Kenney et al. |
| 2011/0180757 | A1 † | 7/2011 | Vockic |
| 2011/0284072 | A1 † | 11/2011 | Takayasu |
| 2012/0031483 | A1 | 2/2012 | Obana et al. |
| 2012/0048357 | A1 | 3/2012 | Hayase et al. |
| 2012/0146007 | A1* | 6/2012 | Snaith .................. H01L 51/422 257/40 |
| 2012/0305918 | A1 | 12/2012 | Shum |
| 2012/0306053 | A1 | 12/2012 | Shum et al. |
| 2013/0139872 | A1 | 6/2013 | Shum et al. |
| 2013/0233377 | A1 | 9/2013 | Kanatzidis et al. |
| 2013/0319529 | A1 | 12/2013 | Tsuda et al. |
| 2013/0320836 | A1 | 12/2013 | Kanatzidis et al. |
| 2015/0136232 | A1 | 5/2015 | Snaith et al. |
| 2015/0144196 | A1 | 5/2015 | Irwin et al. |
| 2015/0200377 | A1* | 7/2015 | Etgar .................. H01L 51/4226 136/256 |
| 2015/0249170 | A1 | 9/2015 | Snaith et al. |
| 2015/0295194 | A1 | 10/2015 | Kanatzidis et al. |
| 2015/0340632 | A1 | 11/2015 | Etgar |

FOREIGN PATENT DOCUMENTS

| | | |
|---|---|---|
| EP | 2693503 | 2/2014 |
| GB | 957191 | 5/1964 |
| JP | 05279009 A | 10/1993 |
| JP | 2003142168 | 5/2003 |
| KR | 10-20080079894 | 9/2008 |
| KR | 10-20110066382 | 6/2011 |
| WO | WO 2013/129097 | 9/2013 |
| WO | WO 2013/171518 | 11/2013 |
| WO | WO 2013/171520 | 11/2013 |
| WO | WO 2013171517 | 11/2013 |

OTHER PUBLICATIONS

International Search Report & Written Opinion mailed on Jul. 14, 2015, for Intl. Patent Appl. No. PCT/US2015/025802, 11 pp.
International Search Report & Written Opinion mailed on Jul. 23, 2015, for Intl. Patent Appl. No. PCT/US2015/027501, 12 pp.
Papavassiliou et al., Excitonic Bands in the Photoconductivity Spectra of Some Organic-Inorganic Hybrid Compounds Based on Metal Halide Units, International Journal of Modern Physics B, vol. 15, Nos. 28, 29 & 30, 2001, pp. 3727-3731.
Shum et al., Synthesis and characterization of CsSnI3 thin films, Applied Physics Letters, vol. 96, No. 221903, Jun. 2, 2010, pp. 1-3.
International Search Report and Written Opinion issued in PCT/US2013/026827, Jun. 14, 2013.
International Search Report and Written Opinion issued in PCT/US2013/027087, Jun. 21, 2013.
Yamada et al., Structure and Bonding of Two Modifications of CsSnI3 by Means of Powder X-Ray Diffraction, 1271 NQR, and DTA, Chemistry Letters, 1989, pp. 1325-1328.
Yamada et al., Structural Phase Transitions of the Polymorphs of CsSnI3 by Means of Rietveld Analysis of the X-Ray Diffraction, Chemistry Letters, 1991, pp. 801-804.
Trots et al., High-temperature structural evolution of caesium and rubidium triiodoplumbates, Journal of Physics and Chemistry of Solids, vol. 69, 2008, pp. 2520-2526.
Takahashi et al., Charge-transport in tin-iodide perovskite CH3NH3SnI3: origin of high conductivity, Dalton Transactions, vol. 40, Apr. 14, 2011, pp. 5563-5568.
Yamada et al., Tunable Perovskite Semiconductor CH3NH3SnX3 (X: Cl, Br, or I) Characterized by X-ray and DTA, Bull. Chem. Soc. Jpn., vol. 84, No. 9, Aug. 27, 2011, pp. 926-932.
Papavassiliou et al., Structural, optical and related properties of some natural three- and lower-dimensional semiconductor systems, Synthetic Metals, vol. 71, 1995, pp. 1713-1714.
D. Mitzi, Synthesis, Crystal Structure, and Optical and Thermal Properties of (C4H9NH3)2MI4 (M ) Ge, Sn, Pb), Chem. Mater., vol. 8, 1996, pp. 791-800.
G.C. Papavassiliou, Three- and Low-Dimensional Inorganic Semiconductors, Prog. Solid St. Chem., vol. 25, 1997, pp. 125-270.
Billing et al., Inorganic-organic hybrid materials incorporating primary cyclic ammonium cations: The lead bromide and chloride series, CrystEngComm, vol. 11, May 18, 2009, pp. 1549-1562.
Mercier et al., Structural diversity and retro-crystal engineering analysis of iodometalate hybrids, CrystEngComm, vol. 11, 2009, pp. 720-734.
Wu et al., Structural overview and structure-property relationships of iodoplumbate and iodobismuthate, Coordination Chemistry Reviews, vol. 253, Aug. 12, 2009, pp. 2787-2804.
Mitzi et al., Conducting tin halides with a layered organic-based perovskite structure , Nature, vol. 369, Jun. 9, 1994, pp. 467-469.
Mitzi et al., Transport, Optical, and Magnetic Properties of the Conducting Halide Perovskite CH3NH3SnI3, Journal of Solid State Chemistry, vol. 114, 1995, pp. 159-163.
Mitzi et al., Synthesis, Resistivity, and Thermal Properties of the Cubic Perovskite NH2CH5NH2SnI3 and Related Systems, Journal of Solid State Chemistry, vol. 134, 1997, pp. 376-381.
Calabrese et al., Preparation and Characterization of Layered Lead Halide Compounds , J. Am. Chem. Soc., vol. 113, 1991, pp. 2328-2330.
Chung et al., CsSnI3: Semiconductor or Metal? High Electrical Conductivity and Strong Near-Infrared Photoluminescence from a Single Material. High Hole Mobility and Phase-Transitions, J. Am. Chem. Soc., vol. 134, May 11, 2012, pp. 8579-8587.
Tanaka et al., Comparative study on the excitons in lead-halide-based perovskite-type crystals CH3NH3PbBr3 CH3NH3PbI3, Solid State Communications, vol. 127, 2003, pp. 619-623.
Im et al., 6.5% efficient perovskite quantum-dot-sensitized solar cell, Nanoscale, vol. 3, Sep. 7, 2011, pp. 4088-4093.
Chung et al., All-solid-state dye-sensitized solar cells with high efficiency, Nature, vol. 485, May 24, 2012, pp. 486-490.
Etgar et al., Mesoscopic CH3NH3PbI3/TiO2 Heterojunction Solar Cells, J. Am. Chem. Soc., vol. 134, Oct. 8, 2012, pp. 17396-17399.

(56) References Cited

OTHER PUBLICATIONS

Lee et al., Efficient Hybrid Solar Cells Based on Meso-Superstructured Organometal Halide Perovskites, Science, vol. 338, Nov. 2, 2012, pp. 643-647.

Scaife et al., Crystal Preparation and Properties of Cesium Tin(II) Trihalides, Journal of Solid State Chemistry, vol. 9, 1974, pp. 308-314.

Yu et al., Temperature dependence of the band gap of perovskite semiconductor compound $CsSnI_3$, Journal of Applied Physics, vol. 110, No. 063526, Sep. 27, 2011, pp. 1-5.

Chen et al., Photoluminescence study of polycrystalline $CsSnI_3$ thin films:Determination of exciton binding energy, Journal of Luminescence, vol. 132, Sep. 10, 2011, pp. 345-349.

Poglitsch et al., Dynamic disorder in methylammoniumtrihalogenoplumbates (II) observed by millimeterwave spectroscopy, J. Chem. Phys., vol. 87, 1987, pp. 6373-6378.

Xu et al., Molecular Motions and Phase Transitions in Solid $CH_3NH_3PbX_3$ (X=Cl, Br, I) as Studied by NMR and NQR, Z. Naturforsch, vol. 46a, 1991, pp. 240-246.

Onoda-Yamamuro et al., p-T Phase Relations of $CH_3NH_3PbX_3$ (X=Cl, Br, I) Crystals, J. Phys. Chem. Solids, vol. 53, No. 2, 1992, pp. 277-281.

Howie et al., The Crystal Structure of Tin(II) Iodide, Acta Crystallographica, Sect. B, vol. 28, 1972, pp. 2965-2971.

G. Sheldrick, A short history of SHELX, Acta Crystallographica, Sect. A, vol. 64, 2008, pp. 112-122.

Howard et al., Group-Theoretical Analysis of Octahedral Tilting in Perovskites, Acta Crystallographica, Sect. B, vol. 54, 1998, pp. 782-789.

Howard et al., Octahedral tilting in cation-ordered perovskites—a group-theoretical analysis, Acta Crystallographica, Sect. B, vol. 60, 2004, pp. 674-684.

Howard et al., Structures and phase transitions in perovskites—a group-theoretical approach, Acta Crystallographica, Sect. A, vol. 61, 2005, pp. 93-111.

Swainson et al., Orientational ordering, tilting and lone-pair activity in the perovskite methylammonium tin bromide, $CH_3NH_3SnBr_3$, Acta Crystallographica, Sect. B, vol. 66, 2010, pp. 422-429.

Borriello et al., Ab initio investigation of hybrid organic-inorganic perovskites based on tin halides, Physical Review B, vol. 77, No. 235214, Jun. 23, 2008, pp. 1-9.

Kojima et al., Organometal Halide Perovskites as Visible-Light Sensitizers for Photovoltaic Cells, J. Am. Chem. Soc., vol. 131, 2009, pp. 6050-6051.

M. Gratzel, Recent Advances in Sensitized Mesoscopic Solar Cells, Accounts of Chemical Research, vol. 42, No. 11, Nov. 2009, pp. 1788-1798.

Yanagida et al., Iodine/Iodide-Free Dye-Sensitized Solar Cells, Accounts of Chemical Research, vol. 42, No. 11, Nov. 2009, pp. 1827-1838.

Wang et al., An organic redox electrolyte to rival triiodide/iodide in dye-sensitized solar cells, Nature Chemistry, vol. 2, Apr. 4, 2010, pp. 385-389.

Mitzi et al., Conducting Layered Organic-Inorganic Halides Containing (110)-Oriented Perovskite Sheets, Science, vol. 267, Mar. 10, 1995, pp. 1473-1476.

Lee et al., Air-Stable Molecular Semiconducting Iodosalts for Solar Cell applications: $Cs_2 SnI_6$ as a hole conductor, J. Am. Chem. Soc. 136, Oct. 9, 2014, pp. 15379-15385.

Stoumpos et al. Semiconducting Tin and Lead Iodide Perovskite with Organic Cations: Phase Transitions, High Mobilities, and Near-Infrared Photoluminescent Properties, Inorg. Chem. 52, Jul. 8, 2013, pp. 9019-9038.

Kojima et al., "Organometal Halide Perovskites as Visible-Light Sensitizers for Photovoltaic Cells" J. Am. Chem. Soc. 131, pp. 6050-6051 (2009).†

Kojima et al., "Novel Photoelectrochemical Cell with Mesoscopic Electrodes Sensitized by Lead-halide Compounds (11)" 214th ECS Meeting, Abstract #27, The Electrochemical Society (Oct. 13, 2008).†

Li et al., "Photoconductive Properties of Organic-Inorganic Hybrid Perovskite $(C6H13NH3)_2$ $(CH3NH3)m-1PbmI3m+1:TiO_2$ Nanocomposites Device Structure" Materials Letters 64, pp. 2735-2737 (2010).†

Akihiro Kojima et al., Organometal Halide Perovskites as Visible-Light Sensitizers for Photovoltaic Cells, J. Am. Chem. Soc. 131, 6050-6051, 2009.†

D. B. Mitzi et al., Transport, Optical, and Magnetic Properties of the Conducting Halide Perovskite $CH_3NH_3SnI_3$, J. Solid State Chem. 114, 159-163, 1995.†

\* cited by examiner
† cited by third party

LIQUID ELECTROLYTE-FREE, SOLID-STATE SOLAR CELLS WITH INORGANIC HOLE TRANSPORT MATERIALS

CROSS-REFERENCE TO RELATED APPLICATIONS

This application claims priority from U.S. provisional patent application Ser. No. 61/601,262, filed on Feb. 21, 2012, and from U.S. provisional patent application Ser. No. 61/601,219, filed on Feb. 21, 2012, both of which are incorporated herein by reference.

REFERENCE TO GOVERNMENT RIGHTS

This invention was made with government support under DE-FG02-08ER46536, DE-SC0001059 awarded by the Department of Energy, and DMR0843962 and ESI0426328 awarded by the National Science Foundation. The government has certain rights in the invention.

BACKGROUND

Dye-sensitized solar (DSCs) cells are low-cost photovoltaic devices that can provide high solar energy conversion efficiencies. Conventional DSCs consist of a wide band gap semiconductor oxide (e.g., $TiO_2$, $SnO_2$ or ZnO), Ru complex photosensitizing dye molecules loaded onto the semiconductor oxide, electrolytes containing $I^-/I_3^-$ redox couples in organic solvents and Pt-coated counter electrode. The role of the electrolyte is to transfer electrons to the photosensitizing dye molecules and also to transport the positive charges to the counter electrode. High conversion efficiency, long-term stability and facile and low-cost fabrication are essential for commercialization of DSCs. Unfortunately, iodide-containing electrolytes commonly used in DSCs are highly corrosive and volatile, resulting in reduced cell performance control, reduced long-term durability and incompatibility with some metallic components, such as Ag, in the presence of water and oxygen.

Research focused on replacing conventional fluid electrolytes for DSCs with p-type semiconductors and solid-state hole-transport materials (HTMs) has been conducted. These alternative electrolyte materials are mostly organic molecules, such as sprio-OMeTAD (2,2',7,7'-tetranis(N,N-di-p-methoxyphenyl-amine)9,9'-spirobifluorene) and p-type conducting polymers, such as polypyrole, polydiacetylene, poly (3-octylthiophene), poly(3,4-ethylenedioxythiophene) (PEDOT) and 2,2'-bis(3,4-ethylenedioxythiophene) (bis-EDOT). As an organic HTM, spiro-OMeTAD has shown an efficiency of $\eta=5.1\%$. As a conducting polymer HTM, (bis-EDOT) with Z907 dye provided an efficiency of $\eta=6.1\%$. A DSC with an iodide-free, organic redox electrolyte of disulfide/thiolate molecules has shown an efficiency of $\eta=6.4\%$.

Despite many advantages, inorganic HTMs are uncommon. Examples are CuI, CuSCN and NiO. The efficiency of CuI-based DSCs has been reported to be about 6%. However, formation of $Cu_2O/CuO$ and the release of iodine on standing rapidly degraded $CuI/TiO_2$ interfaces. Cells of CuSCN showed an efficiency of about 2%. P-type NiO particles exhibited very poor performance as a hole transport layer.

SUMMARY

Materials comprising inorganic compounds, which are referred to as A/M/X compounds are provided. Also provided are photovoltaic cells, including dye sensitized solar cells, pn-junction photovoltaic cells and organic photovoltaic cells, incorporating the compounds as hole transport materials.

The A/M/X compounds comprise one or more A moieties, one or more M atoms and one or more X atoms. In some embodiments, where the A moieties are selected from organic cations and elements from Group 1 of the periodic table, the M atoms are selected from elements from at least one of Groups 3, 4, 5, 13, 14 or 15 of the periodic table, and the X atoms are selected from elements from Group 17 of the periodic table. In other embodiments, the compounds are chalcogenides or chalcohalides where the A moieties are selected from organic cations and elements from Group 1 of the periodic table, the M atoms are selected from elements from at least one of Groups 3, 4, 5, 13, 14, 15 or 16 of the periodic table, and the X atoms are selected from elements from at least one of Groups 16 or 17 of the periodic table, wherein at least one element from Group 16 is present.

In the A/M/X compounds, M may represent two or more different M atoms (i.e., different M elements) and/or X may represent two or more different X atoms (e.g., different halogen elements). By way of illustration, the A/M/X compound may be a mixed halide comprising both I and F atoms or a mixed halide comprising both I and Br atoms. The present materials may be single-phase materials or multi-phase materials. For example, the materials may comprise a first phase comprising the A/M/X compound doped with a second phase comprising, for example, a metal halide or a metal oxide.

In some embodiments, the materials are characterized by one or more of the following properties: (a) a work function of at least 5.5 eV; (b) an energy band gap in the range of 0.8-2.0 eV; and (c) a carrier mobility of at least $10^{-3}$ $cm^2$/V-sec. In addition, the materials may be processed and deposited into a thin film from a solution or a vapor.

In some embodiments, the A/M/X compounds have a formula $AMX_3$, where A is a Group 1 element, M is a Group 14 element (or more than one Group 14 element) and X is a Group 17 element (or more than one Group 17 element). In other embodiments, the A/M/X compounds have a formula $AMX_3$, where A is an organic cation, such as a monovalent organic ammonium cation, M is a Group 14 element (or more than one Group 14 element) and X is a Group 17 element (or more than one Group 17 element). Thus, in some members of this embodiment, wherein the A/M/X compound comprises two X elements, the compound has the formula $AMX_{(3-x)}X'_x$, where X and X' are different halogen atoms and $0.01<x<0.99$. In some members of this embodiments, the material is a two-phase material comprising a first phase of $AMX_{(3-x)}X'_x$ and a second phase comprising a dopant compound, such as a metal halide dopant (e.g., $SnF_2$) or a metal oxide dopant.

Examples of compounds having the formula $AMX_3$ include, $CsSnI_3$; $CsSnI_{(3-x)}F_x$; doped with a metal halide such as $SnF_2$; $CsSnBr_3$; $CsSnI_{(3-x)}Br_x$; and $CsSnI_{(3-x)}Br_x$ doped with a metal halide such as $SnF_2$.

In some embodiments, the A/M/X compounds have a formula selected from $A_2MX_4$, $AM_2X_5$, $A_2MX_6$ or $AMX_5$, where A is a Group 1 element, M is a Group 14 element and X is a Group 17 element. In other embodiments, the A/M/X compounds have a formula selected from $AMX_3$, $A_2MX_4$, $AM_2X_5$, $A_2MX_6$ or $AMX_5$, where A is an organic cation, M is a Group 14 element and X is a Group 17 element. As in the $AMX_3$ compounds, the $A_2MX_4$, $AM_2X_5$, $A_2MX_6$ and $AMX_5$ compounds may comprise two or more different X elements. Also, like the $AMX_3$ compounds, the $A_2MX_4$, $AM_2X_5$, $A_2MX_6$ and $AMX_5$ compounds may be doped to provide a two-phase material comprising a first phase of the $A_2MX_4$, $AM_2X_5$, $A_2MX_6$ or $AMX_5$ and a second phase comprising a dopant compound, such as a metal halide dopant or a metal oxide dopant.

The A/M/X compounds in the present materials can be mixed with one or more congener compounds.

The A/M/X compounds can be doped with a dopant selected from main group elements, transition metal elements, lanthanide elements, actinide elements or compounds comprising one of more of said elements.

In some embodiments, the A/M/X compounds are binary or ternary metal chalcogenides where one of the elements is a chalcogen selected from Te, Se, and S.

In some embodiments, the A/M/X compounds are binary or ternary metal oxides where one of the elements is oxygen.

In some embodiments, the A/M/X compounds are ternary metal chalcogenide halides (chalcohalides), where one of the elements is a chalcogen selected from Te, Se, and S and one of the elements is halogen selected from F, Cl, Br, and I.

Photovoltaic cells incorporating the A/M/X compounds as an HTM can take on a variety of forms. Generally, however, the cells will comprises a first electrode comprising an electrically conductive material, a second electrode comprising an electrically conductive material, a photoactive material (that is—a material capable of absorbing radiation and generating an electron-hole pair) disposed between (including partially between) and in electrical communication with the first and second electrodes, and a hole transporting material comprising an A/M/X compound disposed between the first and second electrodes and configured to facilitate the transport of holes (that is, to provide preferential transport of holes relative to electrons) generated in the photoactive material to one of the first or second electrodes. In some cells, the hole transporting material may itself serve as a photoactive material. In some cells the photoactive material takes the form of a porous film (e.g., a film comprising a collection of nanoparticles, such as titanium dioxide nanoparticles) and the hole tran material takes the form of a coating on the hole transporting material that infiltrates into the pores of the porous film. At least one of the two electrodes is desirably transparent to the incident radiation. The transparent nature of the electrode can be accomplished by constructing the electrode from a transparent material or by using an electrode that does not completely cover the incident surface of the cell (e.g., a patterned electrode).

A dye-sensitized solar cell incorporating an A/M/X compound as an HTM comprises: (a) a photoanode comprising a porous film of semiconductor oxide coated on a first transparent conducting oxide substrate, wherein the porous film of semiconductor oxide has a photosensitizing dye adsorbed thereon; (b) a counter electrode comprising an electrically conducting material; and (c) a hole transport material comprising an A/M/X compound disposed between, and in electrical communication with, the porous film of semiconductor oxide and the counter electrode. In such cells, the hole transport material can penetrate the absorbed dye layer and infiltrate the pores of the porous semiconductor oxide film.

A basic pn-junction photovoltaic cell design can also be employed. This type of cell is similar in structure to the dye-sensitized cell, but does not include the photosensitizing dye molecules. A pn-junction photovoltaic cell incorporating an A/M/X compound as an HTM comprises: (a) a first electrode comprising an electrically conducting material; (b) a second electrode comprising an electrically conducting material; (c) a photoactive, n-type semiconductor material; and (d) a hole transporting material comprising a p-type semiconducting A/M/X compound in contact with the n-type semiconductor material at the interface(s) between the two materials, such that a pn-junction is formed at said interface(s); wherein the photoactive material and the hole transporting material are disposed between, and in electrical communication with, the first electrode and the counter electrode. Here, again, the n-type semiconductor material desirably takes the form of a porous film and the hole transporting material desirably takes the form of a coating that penetrates into the pores of the film to provide a large surface area interface between the two materials.

An organic photovoltaic cell incorporating an A/M/X compound as an HTM comprises: (a) a first electrode comprising an electrically conducting material; (b) a second electrode comprising an electrically conducting material; (c) a photoactive material comprising a photoactive organic polymer disposed between, and in electrical communication with, the first and second electrodes; and (d) a hole transporting material comprising an A/M/X compound, wherein the hole transporting material is disposed between the first and second electrodes and configured to facilitate the transport of holes generated in the photoactive material to one of the first or second electrodes. By way of illustration only, a poly(3-hexathiophene) and [6,6]-phenyl C61-butyric acid methylester blend (P3HT-PCMB) can be used as a photoactive organic polymer. The organic photovoltaic cells may also include an electron transporting material (ETM) disposed between the first and second electrodes and configured to facilitate the transport of electrons generated in the photoactive material to the other of the first or second electrodes.

It is possible to form materials comprising the A/M/X compounds into thin, conformal coatings by using solution processing methods. Such a solution-based film deposition process for A/M/X compounds comprising the steps of: forming a solution of an A/M/X compound in a polar organic solvent (in some embodiments the A/M/X compounds are formed in situ in the solution from precursor reactants, such as metal halides); deposing the solution onto a substrate (such as a porous film comprising a photoactive material); and drying the deposited solution, whereby a film comprising the A/M/X compound is formed.

DETAILED DESCRIPTION

A/M/X compounds for use as HTMs in photovoltaic cells are provided. Also provided are photovoltaic cells comprising the HTMs. The designation A/M/X is used to refer to a family of compounds that comprise A moieties (atoms or cations), M atoms and X atoms in various ratios, where A represents an atom from Group 1 of the periodic table or an organic cation, M represents an atom from one of Groups 3, 4, 5, 13, 14 or 15 of the periodic table, and X represents an atom from Group 17 of the periodic table. Alternatively, the A/M/X compound can be a chalcogenide or a chalcohalide, wherein the above-referenced M and/or X atoms are substituted with an atom from Group 16 of the periodic table.

The A/M/X compounds that can be used as HTMs include infrared light emitting materials. In some embodiments, the compounds are medium-bandgap semiconductors with $E_g$ values in the range from 1.1-1.8 eV.

The p-type inorganic semiconductors can be widely used as a hole transport material to replace conventional electrolytes in DSCs. Because they are p-type semiconductors, the A/M/X compounds can also be used as hole transport materials in solid-state p-n junction type solar cells.

Figure 1:
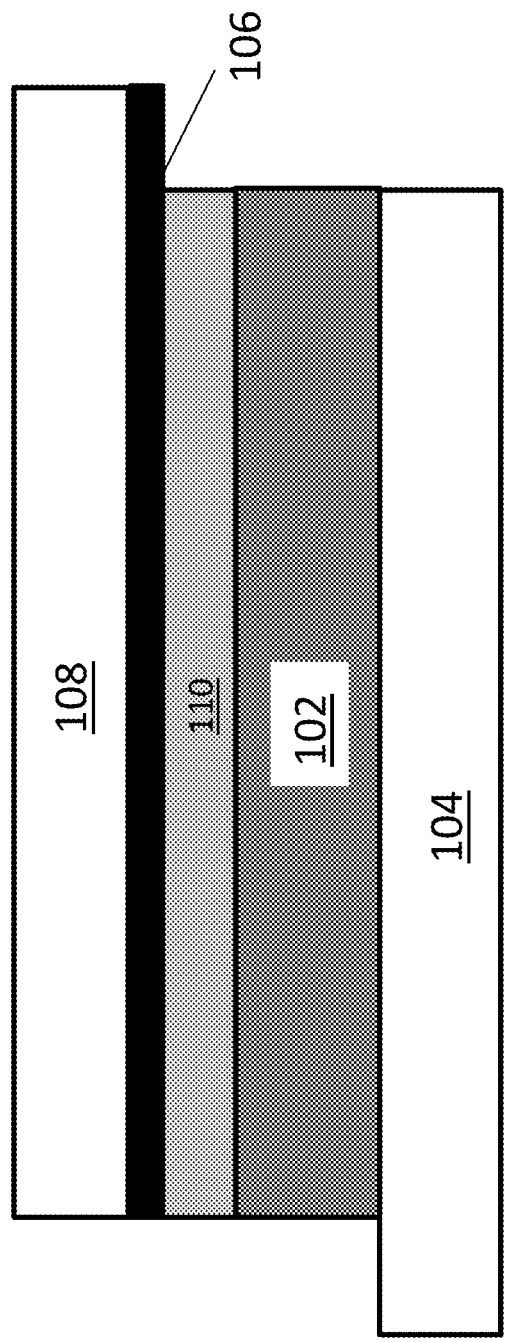
FIG. 1. is a schematic diagram of a cross-section of a DSC comprising $CsSnI_3$ as a solid state HTM.

FIG. 1 shows one embodiment of a structure of a thin-layer DSC. The DSC comprises a photoanode comprising a porous film of semiconductor oxide (e.g., $TiO_2$) 102 coated on a transparent conducting oxide (e.g., FTO) 104. The porous film of semiconductor oxide has a photosensitizing dye adsorbed thereon. The DSC also comprising a counter electrode comprising an electrically conducting metal film (e.g., Pt) 106 disposed on a transparent conducting oxide 108. A hole transport material 110 comprising an A/M/X compound is disposed between, and in electrical communication with, the photoanode and the counter electrode. Hole transport material 110 overlies and impregnates the porous film 102. Example 1 describes a method of making a DSC of the type shown in FIG. 1.

DSCs incorporating the A/M/X compounds as solid state electrolytes can be free of liquid electrolytes and can provide a light to electricity conversion efficiency of 9.7% under AM 1.5 irradiation (100 mW cm$^{-2}$) or better.

Figure 26:
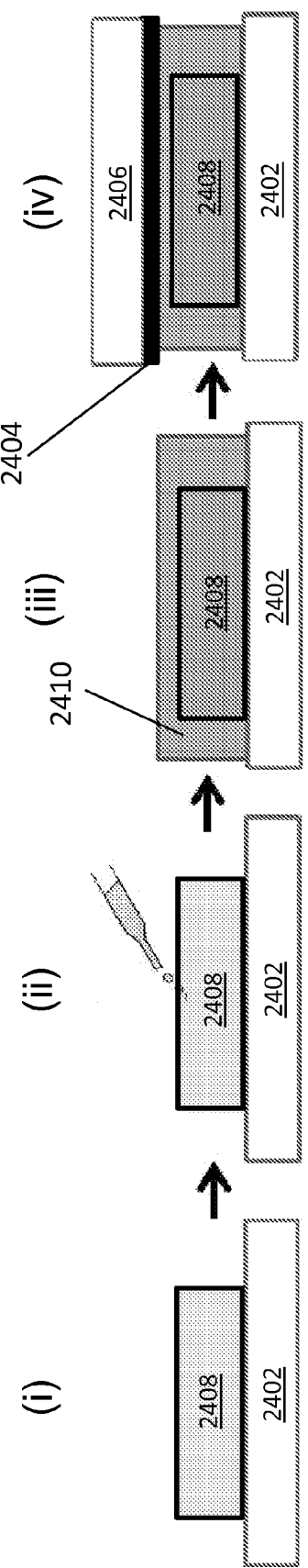
FIG. 26 is a schematic diagram of a cross-section of a pn-junction photovoltaic cell comprising $CsSnI_3$ or $CsSnI_{(3-x)}F_x$ as a solid state HTM. Panels (i)-(iv) in the figure illustrate the fabrication of the cell.

FIG. 26 shows an embodiment of a structure of a pn-junction solar cell. A more detailed description of the solar cell and a method for fabricating the cell is provided in Example 8.

Examples of A/M/X compounds that can be used as HTMs include those having the general formula $AMX_3$, where A is a Group 1 element, M is a Group 14 element and X is a Group 17 element. The p-type semiconductor $CsSnI_3$ and the p-type semiconductor $CsSnI_{2.95}F_{0.05}$, which can be doped with $SnF_2$, are examples of such compounds. However, other A/M/X compounds can also be used, including those with the formulas $AMX_3$, $A_2MX_4$, $AM_2X_5$, $A_2MX_6$ or $AMX_5$, where A, M, and X atoms can be mixed with other congeners (compounds that differ in the number and/or position of the atoms in the structure), for example, $CsSnI_2Cl$ and $Cs_2SnI_2Cl_2$. Doping of the compounds with other main group, transition metal, lanthanide, or actinide elements or their compounds, such as $Al_2O_3$, SnO, $SnF_2$ and $CsSn_{0.5}F_3$ is also possible. Still other HTM materials are described below.

The A/M/X compounds may be classified as, or incorporated into, five types of materials. These types are designated herein as Types I-V.

Type I Materials.

These include A/M/X compounds, such as $CsSnI_3$ or $CsSnBr_3$, that are alloyed with other compounds—particularly with: (A) M(II) oxides or (B) M(IV) hexafluorides. The resulting alloys can exhibit a significant increase in their photoluminescence properties. In addition, alloying of these A/X/M compounds can be used to provide a controlled shift in the emission wavelength of the materials. In some embodiments, the Type I materials are doped and/or alloyed with one or more of M(I) or M(III) oxides, M(I) or M(III) halides, and M(III) or M(V) hexahalides, to provide p- or n-type semiconductors. These, and other, A/M/X compounds may be mixed halides—that is, the X may represent two or more halide elements. In such compounds having a Type I structure, the "X" may represent an $X_{(3-x)}X'_x$ structure, wherein X and X' are different halide atoms.

Type II Materials.

These include two sub-types of materials, Type IIA and Type IIB. In Type IIA materials, the A moiety in the A/M/X compound comprises a monovalent organic cation (A'), examples of which include methylammonium ($CH_3NH_3^+$), formamidinium ($HC(NH_2)_2^+$), methylformamidinium ($H_3CC(NH_2)_2^+$) and guanidinium ($C(NH_2)_3^+$). At least some embodiments of these hybrid organic/inorganic materials are photoluminescent having the general formula $A'MI_3$.

In Type IIB materials, the A moiety in the A/M/X compound comprises a bulky π-conjugated organic dication (A"), examples of which include N,N'-alkyl bipyridines (RV's, where R=H, Me, Et, etc. . . . ) and acridine. Such materials can form phases having the formulas $AMI_3$, $A''MI_4$ or $A''M_2I_6$ capable of producing photoluminescence emission on red light excitation (785 nm).

Type III Materials.

In these materials, the X moiety of the A/M/X compound comprises at least two halides, wherein at least one equivalent of iodide is present. The halide, X, comprise I substituted with any other halide to form $AMIX_2$ phases. These materials include A/M/X compounds in which A=Cs, methylammonium ($CH_3NH_3^+$) or formamidinium ($HC(NH_2)_2^+$); and M=Ge, Sn, or Pb.

Type IV Materials: Germanium Iodides.

In these materials, the M moiety of the A/M/X compound comprises germanium and the X moiety comprises iodine. These germanium(IV) iodide compounds can display photoluminescence on green light irradiation (532 nm). Examples of these materials include those having $AGeI_5$ or $A_2GeI_6$ phases, where A=a Group 1 metal, methylammonium ($CH_3NH_3^+$), formamidinium ($HC(NH_2)_2^+$), methylformamidinium ($H_3CC(NH_2)_2^+$) or guanidinium ($C(NH_2)_3^+$). Ge(II) iodides also display photoluminescence including $GeI_1$, but these are being described in Type II and Type III phases, having the formula $AGeI_3$.

Type V Material.

These materials comprise complex compositions of the general formula $(AMX_3)_x(A'M'X'_3)_y(A''M''X''_3)_x$, where x+y+z=1 and where A, A', A" and M, M', M" and X, X', X" stand for any possible combination of Type I, Type II, Type III and/or Type IV materials.

EXAMPLES

Example 1

This Example illustrates methods of making a DSC comprising $CsSnI_3$ and $CsSnI_{3-x}F_x$ as HTMs. Although this example describes only the preparation and use of $CsSnI_3$ and its related F-doped compounds as HTMs, the same procedures can be readily adapted to provide HTMs comprising other A/M/X compounds.

Materials and Methods.

Preparation of $CsSnI_3$ and Other A/M/X Compounds.

Pure $CsSnI_3$ was prepared by reaching a stoichiometric mixture of CsI and $SnI_2$ in an evacuated pyrex or fused silica tube at an elevated temperature for 1 h, followed by quenching or cooling for 1-3 h to room temperature (~23° C.) (RT). The reaction of the stoichiometric mixture of CsI and $SnI_2$ was carried out at a temperature in the range of 400°-700° C. However, for $AMX_3$ compounds in which A is substituted with an organic cation, a temperature in the range of 150°-200° C. can be used.

Doped $CsSnI_{3-x}F_x$ was prepared by reaching a stoichiometric mixture of CsI, $SnF_2$ and $SnI_2$ in an evacuated pyrex or fused silica tube at an elevated temperature for 1 h, followed by quenching or cooling for 1-3 h to room temperature (~23° C.) (RT). The reaction of the stoichiometric mixture of CsI, $SnF_2$ and $SnI_2$ was carried out at a temperature in the range of 400°-700° C. This process gives either $CsSnI_{(3-x)}F_x$ or $CsSnI_{(3-x)}F_x$+x % $SnF_2$.

$TiO_2$ Electrode Preparation.

High-purity anatase $TiO_2$ nanoparticles (NPs) were obtained by a 2-step autoclaving technique. A quantity of 30 wt. % commercially available $TiO_2$ powders (P25, Degussa) that consisted of ca. 30% rutile and 70% anatase crystalline phases were hydrothermally treated with 10 N NaOH in an autoclave at 130° C. for 20 h, followed by repeated washing with 0.1N $HNO_3$ to reach a pH value of ca. 1.5 following the procedure described in the literature (Tsai, C.-C.; Teng, H. *Chemistry of Materials* 2005, 18, 367-373.). Pure anatase colloidal $TiO_2$ NPs were obtained by autoclaving the low-pH titanate suspension at 240° C. for 12 h. The composition and morphology of the resulting anatase $TiO_2$ NPs were investigated by a field-emission scanning electron microscope (SEM, S4800, Hitachi) equipped with an energy dispersive spectrometer (EDS). The anatase phase was confirmed by X-ray powder diffraction study (D/Max-A, Rigaku). A paste of anatase $TiO_2$ powder was prepared by stirring a mixture of anatase $TiO_2$ NPs (0.5 g), Triton X-100 (100 mL), polyethylene glycol (0.2 g, PEG, Fluka, M.w.=20,000) into acetic acid (3 mL, 0.1 M). The $TiO_2$ paste was spread on a $SnO_2$:F coated glass substrate (Pilkington, TEC 8 glass, 8 Ω/sq, 2.3 mm thick) by the doctor-blade technique to give a flat and smooth surface using adhesive tape spacer. The film thickness was governed by the height of adhesive tape. The exact thickness of the $TiO_2$ film was determined by a surface profiler (Tencor P-10). Finally, the $TiO_2$ coated electrode was gradually calcined to remove the polymer under an air flow at 150° C. for 15 min, at 320° C. for 10 min, and at 500° C. for 30 min, giving a pure anatase $TiO_2$ NP film.

For fluorine etching, the nanoporous $TiO_2$ films were first etched before soaking in the dye solution as described in the literature (Lee, B.; Buchholz, D. B.; Guo, P. J.; Hwang, D. K.; Chang, R. P. H. *Journal of Physical Chemistry C* 2011, 115, 9787-9796.). ZnO photonic crystals were prepared as described in the literature (Lee, B.; Hwang, D. K.; Guo, P. J.; Ho, S. T.; Buchholtz, D. B.; Wang, C. Y.; Chang, R. P. H. *J. Phys. Chem. B* 2010, 114, 14582-14591.).

DSC Assembly.

The next step in the DSC fabrication was to infiltrate the A/M/X HTM materials through the adsorbed dye layer and into the porous $TiO_2$ NP film. First, for photosensitization, the calcined $TiO_2$ NP electrode was immersed in an ethanol solution containing purified $3 \times 10^{-4}$ M cis-di(thiocynato)-N,N'-bis(2,2'-bipyridyl-4-carboxylic acid-4'-tetrabutylammonium carboxylate) ruthenium (II) (N719, Solaronix) for 18 h at RT. The resulting dye-adsorbed $TiO_2$ photoanode was rinsed with ethanol and dried under a nitrogen flow. The counter-electrode was produced by coating $F:SnO_2$ glass with a thin layer of a 5 mM solution of $H_2PtCl_6$ in isopropanol and heating the coated glass at 400° C. for 20 min. The two electrodes were sealed together with thermal melt polymer film (24 μm thick, DuPont). The typical active area of the cell was about 0.3 $cm^2$. The exact area of the photoanode was calibrated by an optical scanner under a resolution of 600 dot per inch (dpi). Next, the A/M/X materials dispersed/dissolved in organic solvents were injected to the cell, followed by drying under $N_2$ and sealing. Alternatively, the dye-loaded $TiO_2$ NP electrode can be immersed in the A/M/X solutions.

JV Characteristics.

The devices were evaluated under 100 mW/$cm^2$ AM 1.5G sunlight simulation with a class A solar cell analyzer (Spectra Nova Tech.). A silicon solar cell fitted with a KG3 filter tested and certified by the National Renewable Energy Laboratory (NREL) was used for calibration. The KG3 filter accounts for the different light absorptions of the dye sensitized solar cell and silicon, and ensures that the spectral mismatch correction factor approaches unity.

TABLE 1

EIS analysis and J-V characteristics of the DSCs comprising $CsSnI_3$, and its doped compounds, as HTMs.

| | | Impedance analysis | | | | | JV characteristics | | | |
|---|---|---|---|---|---|---|---|---|---|---|
| | Area ($cm^2$) | $R_1$ (Ω) | $C_1$ ($10^{-5}$ F) | $R_2$ (Ω) | $C_2$ ($10^{-3}$ F) | $R_{total}$ (Ω) | $V_{OC}$ (V) | $J_{sc}$ (mA/$cm^2$) | FF (%) | η (%) |
| $CsSnI_3$ | 0.290 | 17.9 | 1.54 | 101.9 | 1.6 | 122.0 | 0.638 | 8.82 | 66.1 | 3.72 |
| $CsSnI_{2.95}F_{0.05}$ | 0.290 | 5.72 | 1.04 | 55.7 | 4.0 | 64.0 | 0.649 | 12.2 | 70.7 | 5.62 |
| $CsSnI_{2.95}F_{0.05}$ + 0.02 $SnF_2$ | 0.287 | 5.07 | 3.32 | 42.3 | 4.4 | 49.6 | 0.666 | 15.7 | 65.2 | 6.81 |
| $CsSnI_{2.95}F_{0.05}$ + 0.05 $SnF_2$ | 0.291 | 5.01 | 1.64 | 31.9 | 2.2 | 37.3 | 0.688 | 16.3 | 69.4 | 7.78 |
| $CsSnI_{2.95}F_{0.05}$ + 0.10 $SnF_2$ | 0.302 | 6.03 | 0.99 | 59.2 | 3.9 | 67.8 | 0.654 | 13.6 | 61.4 | 5.46 |

TABLE 2

J-V characteristics of the DSCs comprising an HTM of $CsSnI_3$ doped with 5% $SnF_2$ and an HTM made with an F-etched $TiO_2$ photoanode. The effects of fluorine etching and the presence of stacks of 3-D ZnO photonic crystals (PhCs) are shown. Those with a mask are also presented.

| | | | JV characteristics | | | |
|---|---|---|---|---|---|---|
| | Area ($cm^2$) | $TiO_2$ thickness (μm) | $V_{OC}$ (V) | $J_{sc}$ (mA/$cm^2$) | FF (%) | η (%) |
| $CsSnI_{2.95}F_{0.05}$ + 0.05 $SnF_2$ | 0.291 | 16.3 | 0.688 | 16.3 | 69.4 | 7.78 |
| $CF_4$ etching | 0.263 | 15.2 ± 0.5 | 0.721 | 15.6 | 72.3 | 8.62 |
| With mask | 0.263 | 15.2 ± 0.5 | 0.716 | 13.7 | 75.5 | 7.38 |
| CF4/ZnO PhCs | 0.263 | 15.2 ± 0.5 | 0.725 | 18.1 | 74.4 | 9.74 |
| With mask | 0.263 | 15.2 ± 0.5 | 0.720 | 15.3 | 75.0 | 8.27 |

Results:

The p-type semiconductor $CsSnI_{3-x}F_x$ HTM was prepared by reacting a stoichiometric mixture of CsI, $SnI_2$ and $SnF_2$ at 400° C. for 1 h, followed by quenching to air. The resulting powders were dispersed in acetonitrile and injected into an n-type electrode comprising a nanoporous $TiO_2$ film loaded with a N719 dye. The solutions were rapidly evaporated to form the liquid-free DSCs. A cross-sectional scanning electron microscopy (SEM) image of the $CsSnI_3$ DSC showed that $CsSnI_3$ solution homogeneously permeated deep into the $TiO_2$ films. In addition, a cross-sectional back scattering image showed that the $TiO_2$ and $CsSnI_3$ were well distributed through the cell. This DSC structure is superior to DSC structures that employ conducting polymer HTMs because the penetration depth of the latter is about 4-5 µm, causing poor interfacial properties of the electrode and HTM. Furthermore, the use of polymerization processes in the fabrication of DSCs is complex and unfavorable for large-scale commercialization.

Figure 2:
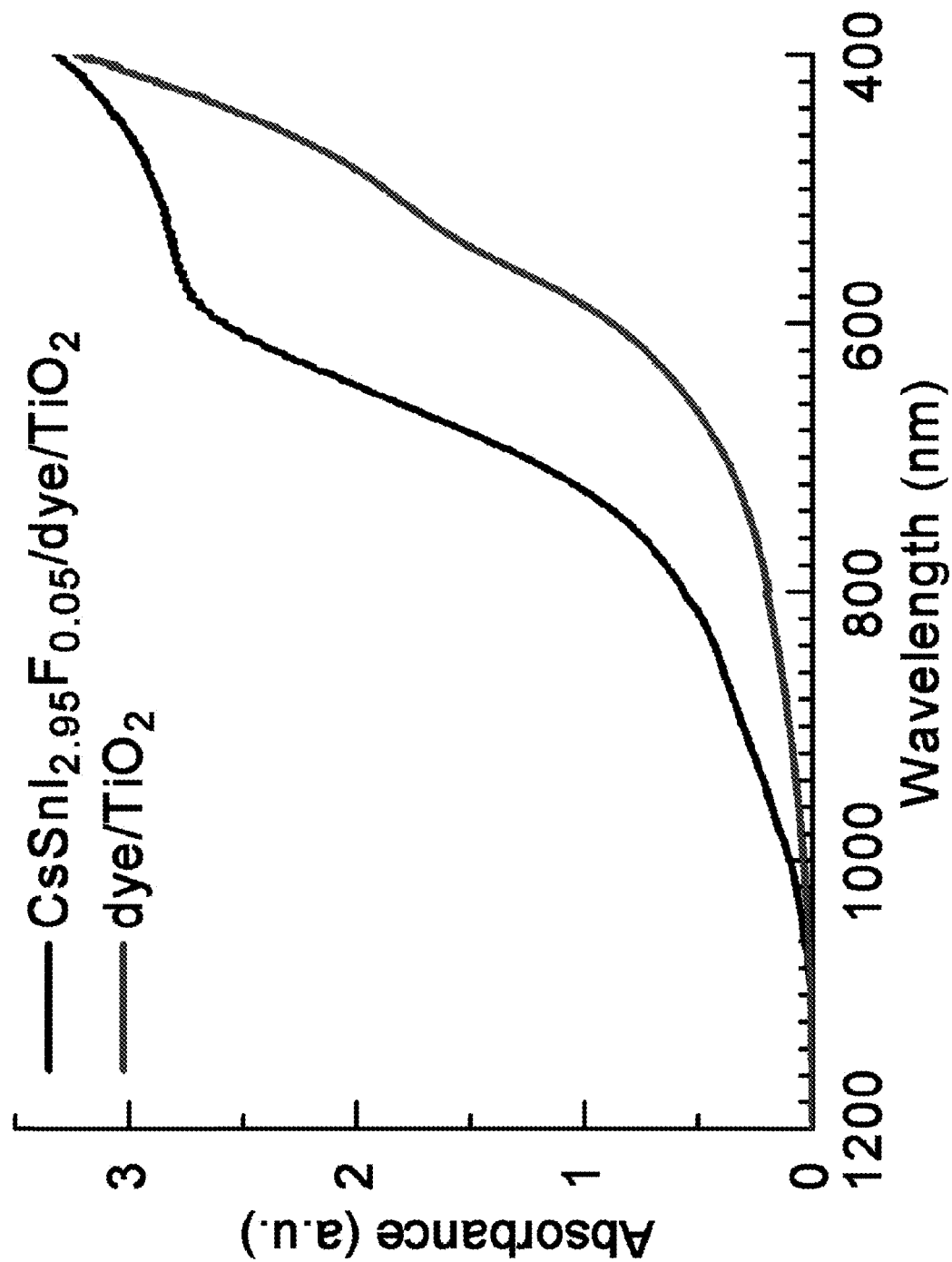
FIG. 2. shows absorbance spectra of DSCs with a photoanode comprising dye-loaded $TiO_2$ (dye/$TiO_2$) and with a photoanode comprising dye-loaded $TiO_2$ with a $CsSnI_{2.95}F_{0.05}$ HTM ($CsSnI_{2.95}F_{0.05}$/dye/$TiO_2$).

The absorbance spectrum of a the DSC comprising $CsSnI_{2.95}F_{0.05}$/dye/$TiO_2$ photoanode compared to that of a DSC comprising a dye/$TiO_2$ photoanode revealed that the former can effectively absorb red and near infrared light with a well-defined absorption edge at 789 nm (FIG. 2). In fact, one of the drawbacks of the Ru dye is its poor performance in such a spectral range.

Figure 3:
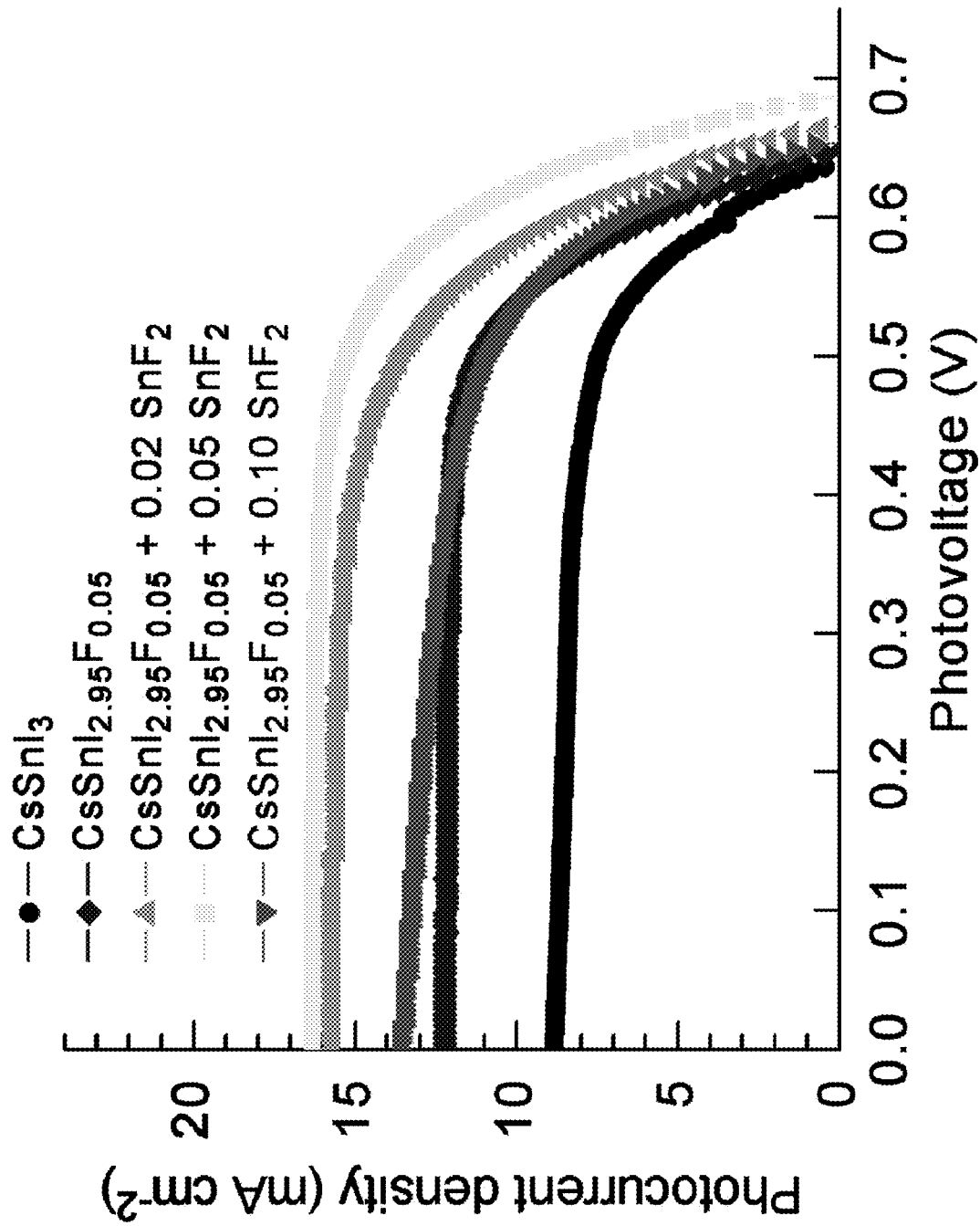
FIG. 3. shows the J-V characteristics of DSCs comprising HTMs of $CsSnI_3$, $CsSnI_{2.95}F_{0.05}$, and $CsSnI_{2.95}F_{0.05}$ doped with $SnF_2$ under irradiation of 100 mW cm$^{-2}$ simulated AM 1.5 sunlight.

FIG. 3 shows the photocurrent density-voltage (J-V) characteristics of the DSCs with the $CsSnI_3$ and $CsSnI_{2.95}F_{0.05}$ HTMs with various amounts of $SnF_2$ doping under 100 m W $cm^{-2}$ AM 1.5 illumination. The detailed photovoltaic parameters of the open circuit voltage ($V_{oc}$), fill factor (FF), short-circuit current density ($J_{sc}$) and photovoltaic conversion efficiency ($\eta$) are given in Table 1. Introducing F atoms into the $CsSnI_3$ significantly improved the photocurrent density. The $J_{sc}$ of the DSC increased from 8.82 mA $cm^{-2}$ to 12.2 mA $cm^{-2}$ when the 5% F-doped material ($CsSnI_{2.95}F_{0.05}$) was used. The $SnF_2$ dopant was introduced to provide a continuous improvement of the $J_{sc}$, which reached the maximum at 16.3 mA $cm^{-2}$ at a doping level of 5% $SnF_2$. As the $J_{sc}$, the efficiency increased. The DSC comprising the HTM $CsSnI_{2.95}F_{0.05}$ doped with 5% $SnF_2$ exhibited the highest efficiency of $\eta$=7.78%.

Figure 4:
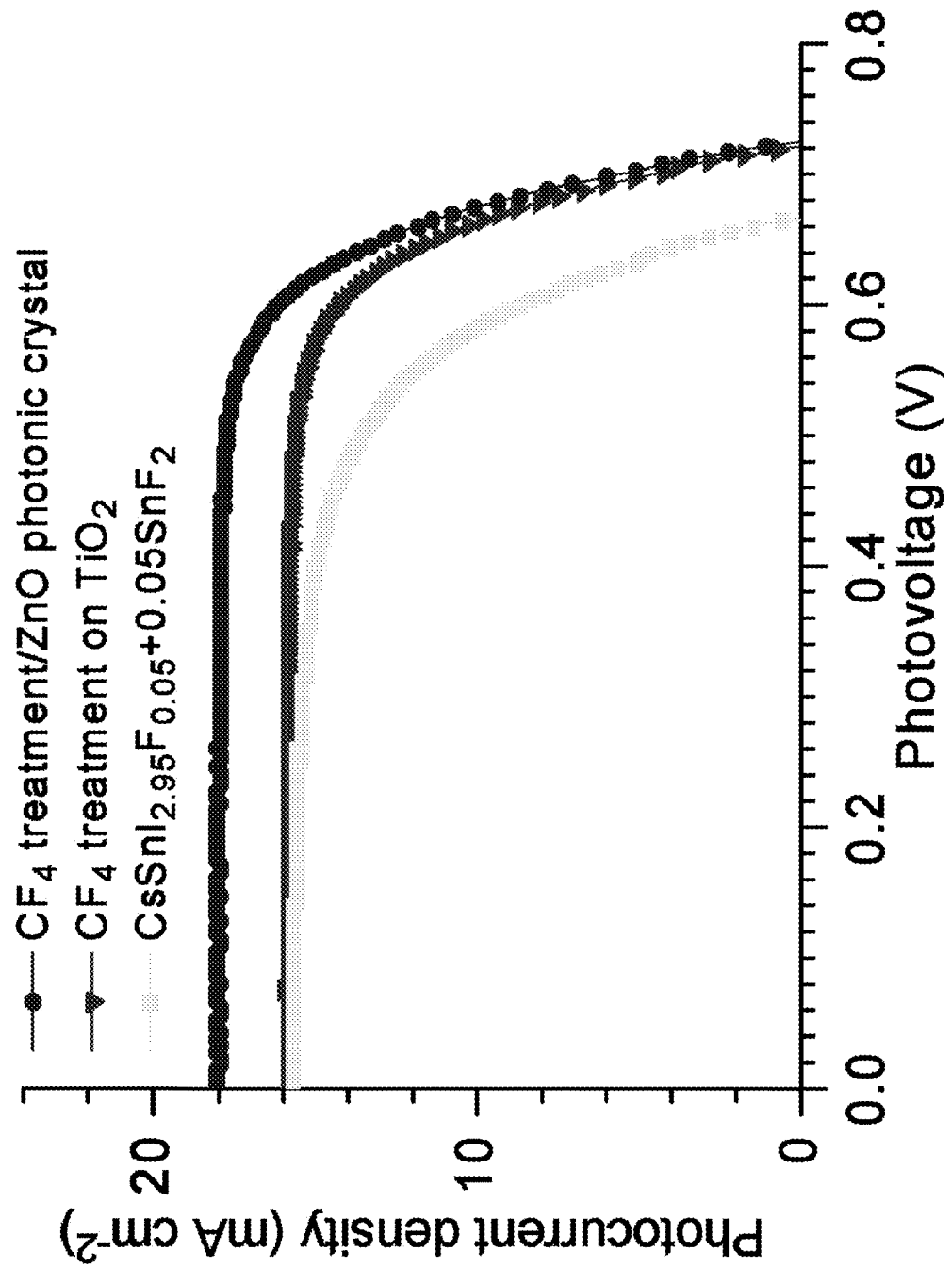
FIG. 4. shows the J-V characteristics of DSCs comprising HTMs of $CsSnI_{2.95}F_{0.05}$ doped with 5% $SnF_2$, the same DSC with a fluorine-etched $TiO_2$, and with stacks of ZnO photonic crystals under irradiation of 100 mW cm$^{-2}$ simulated AM 1.5 sunlight.

To further improve the cell performance, the nanoporous $TiO_2$ films were etched with a fluorine plasma, as described above. This provided an increase in the sizes of the nanopores and nanochannels in the $TiO_2$ films and passivated the surfaces of the nanoporous $TiO_2$. The DSC with $CsSnI_{2.95}F_{0.05}$ HTMs doped with 5% $SnF_2$ using the etched $TiO_2$ film showed an improved efficiency of 8.62% due to a higher $V_{oc}$ of 0.721V and a fill factor of 72.3%, compared to that of a conventional $TiO_2$ film (FIG. 4). The improvement in $V_{oc}$ possibly resulted from the passivation by fluorine etching to remove defect states of $TiO_2$ nanoparticles.

To fully employ the photon flux absorbed, a stack of two 3-D inverse photonic crystals of ZnO were attached to the same DSC, one with hole diameter of 375 nm and another with a hole diameter of 410 nm. The resulting DSC showed a significantly improved $J_{sc}$ of 18.1 mA $cm^{-2}$ to give an efficiency of $\eta$=9.74%. The observed value may be the highest among DSCs with no $I^-/I_3^-$ electrolyte. The J-V characteristics showing the effects of fluorine etching and application of ZnO photonic crystal stacks are shown in Table 2.

Figure 5A:
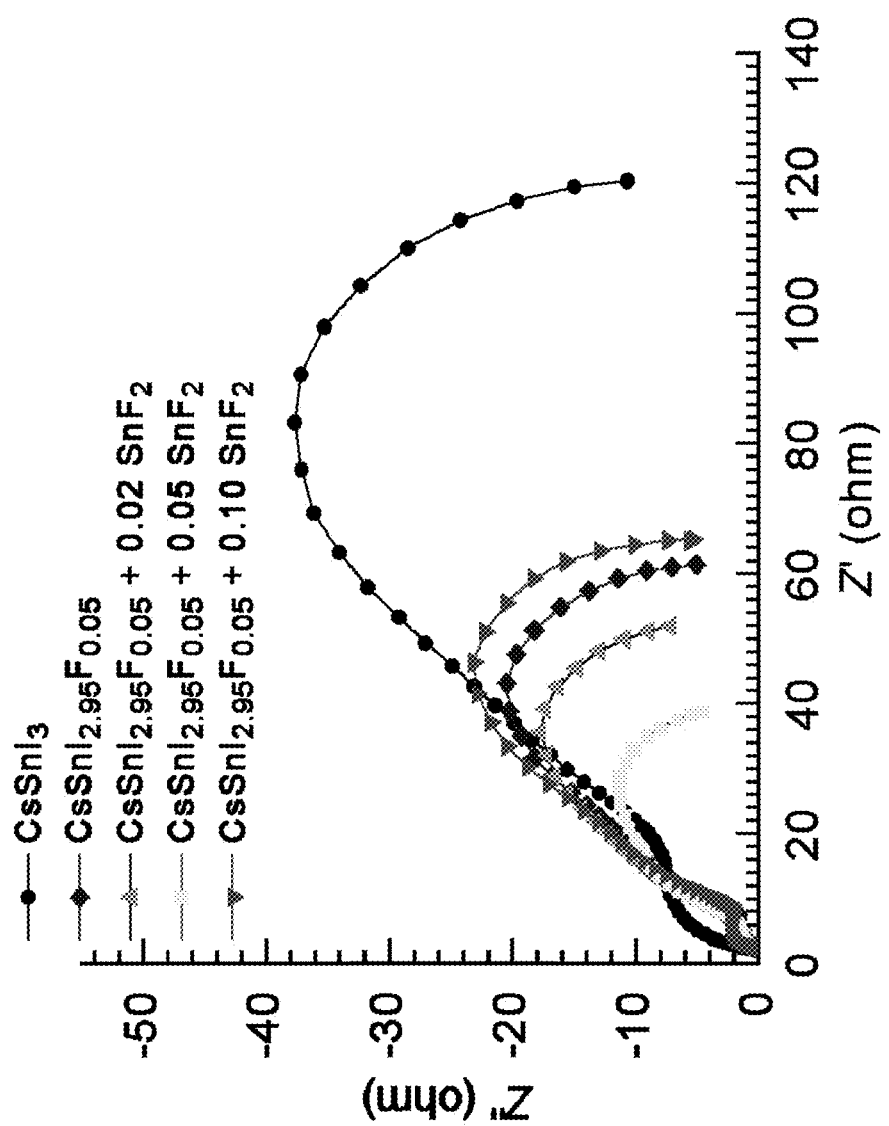
FIG. 5. Electrochemical impedance spectroscopy (EIS) analysis. (A) Nyquist and (B) Bode phase plots. (C) Magnitude of the impedance.
Figure 5B:
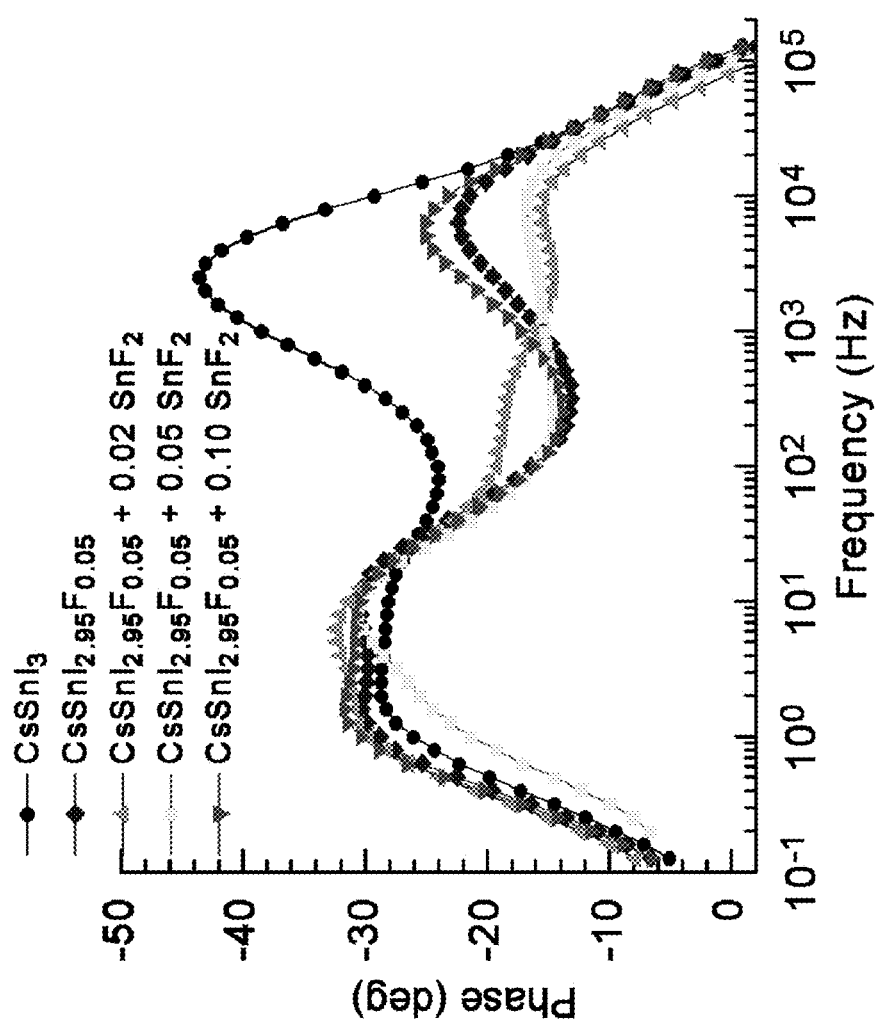
Figure 5C:
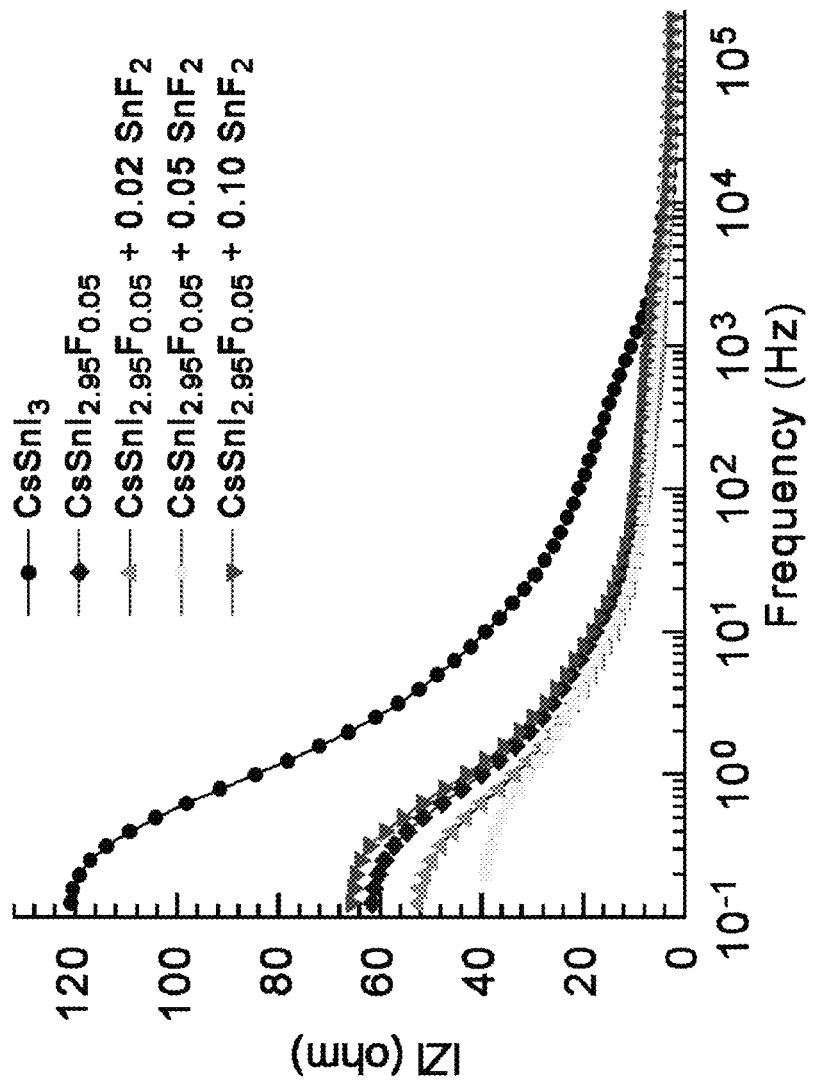
Figure 6:
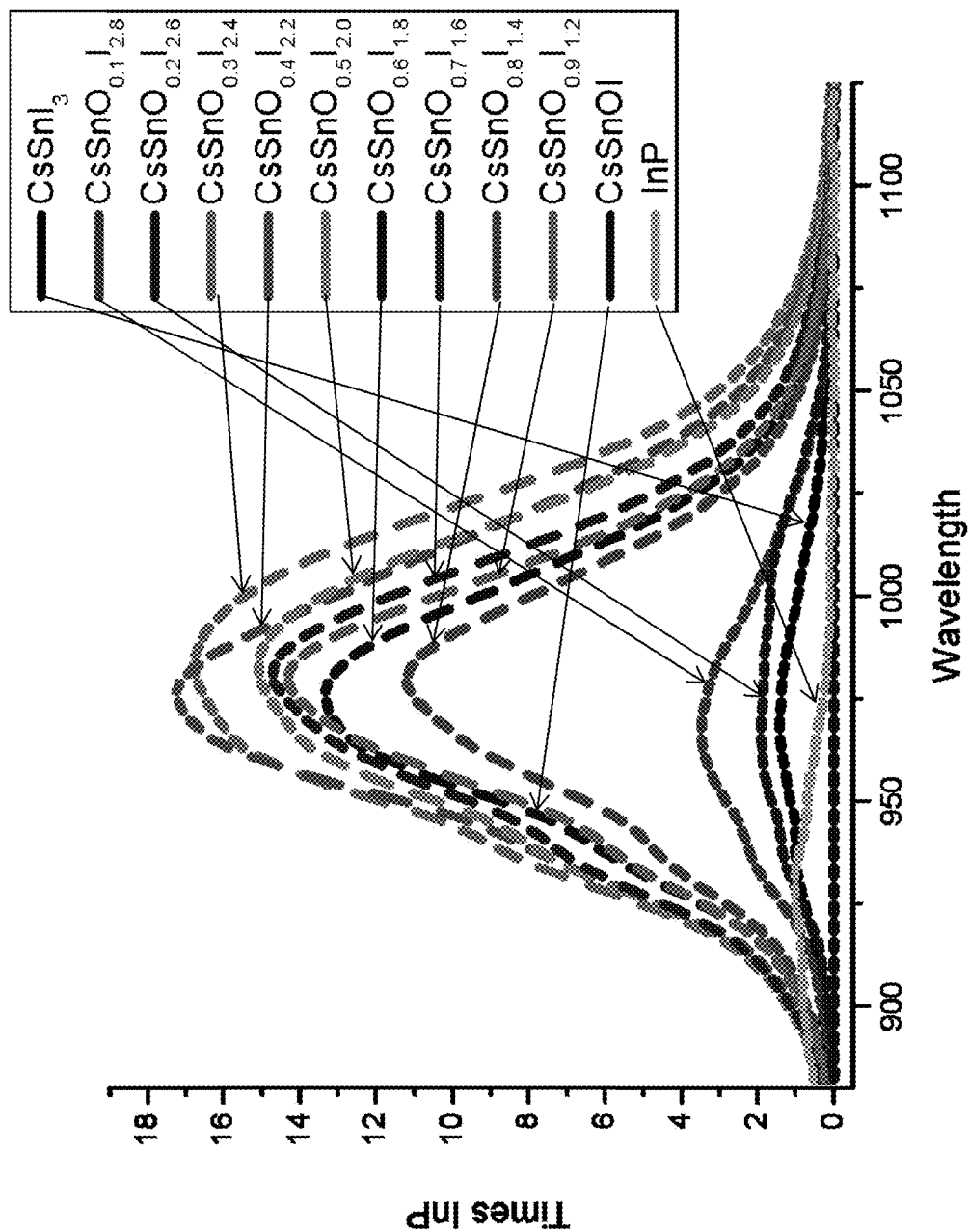
FIG. 6 shows PL spectra for the Type I A/M/X materials, where A is Cs, M is Sn, and X is I.
Figure 7:
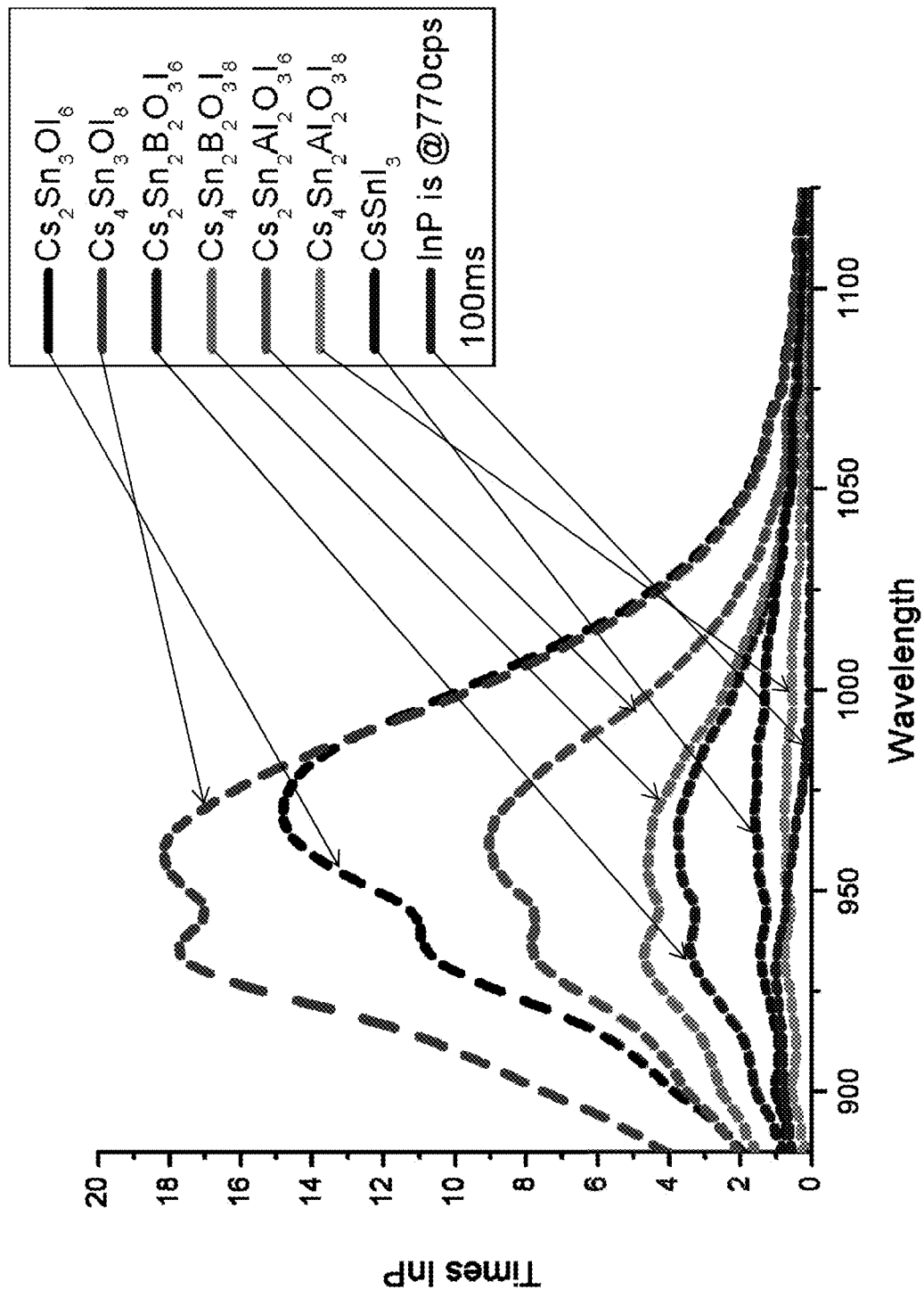
FIG. 7 shows the PL spectra for Type I A/M/X materials, where A is Cs, M is Sn and X is I, including some that are alloyed with oxides.
Figure 8A:
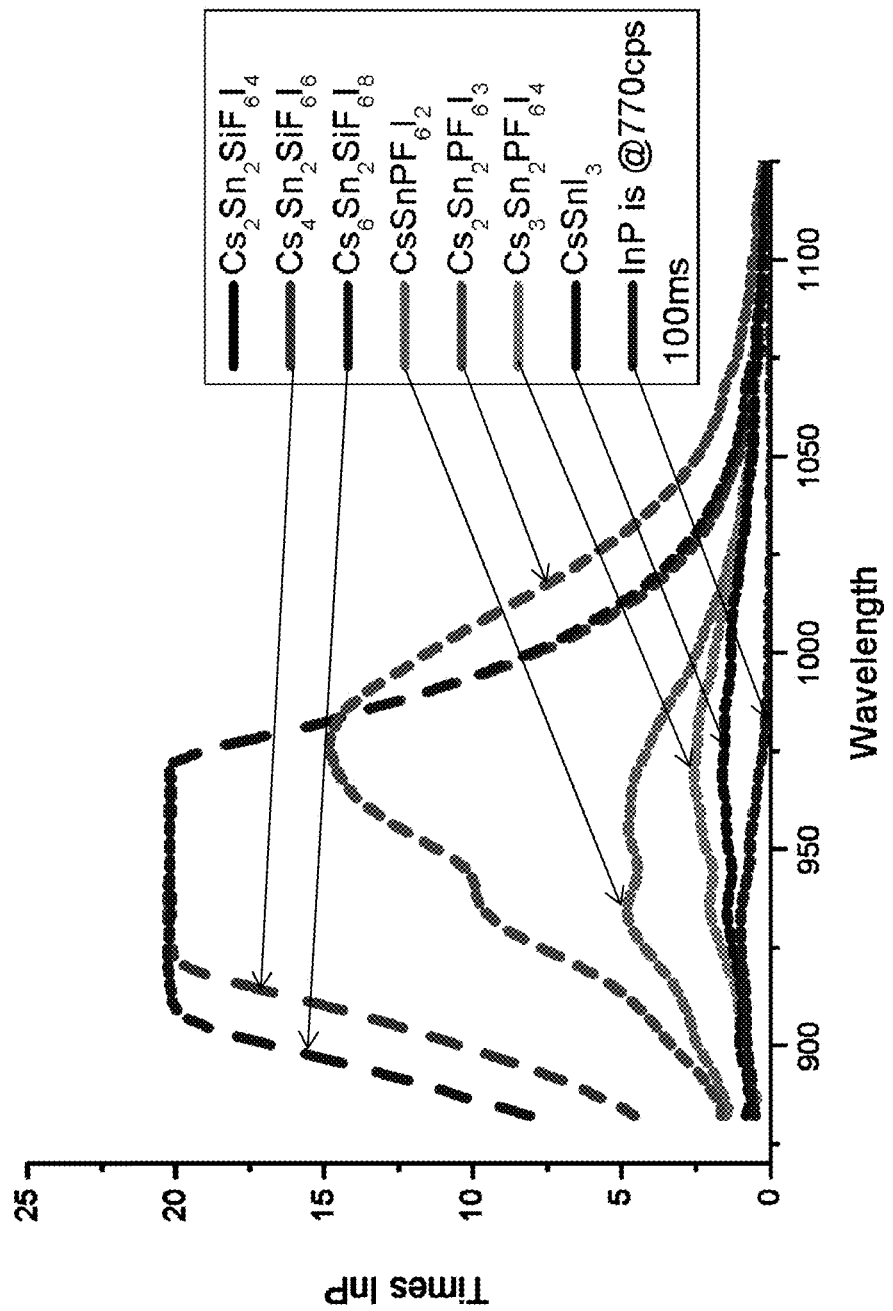
FIG. 8. (A) shows the PL spectra for Type I A/M/X materials, where A is Cs, M is Sn and X is I, including some that are alloyed with hexafluorides. (B) shows the $CS_4Sn_2SiF_6I_6$ phase that saturates the detector, measured at a lower integration time. (C) shows the $CS_6Sn_2SiF_6I_8$ phase that saturates the detector, measured at a lower integration time.
Figure 8B:
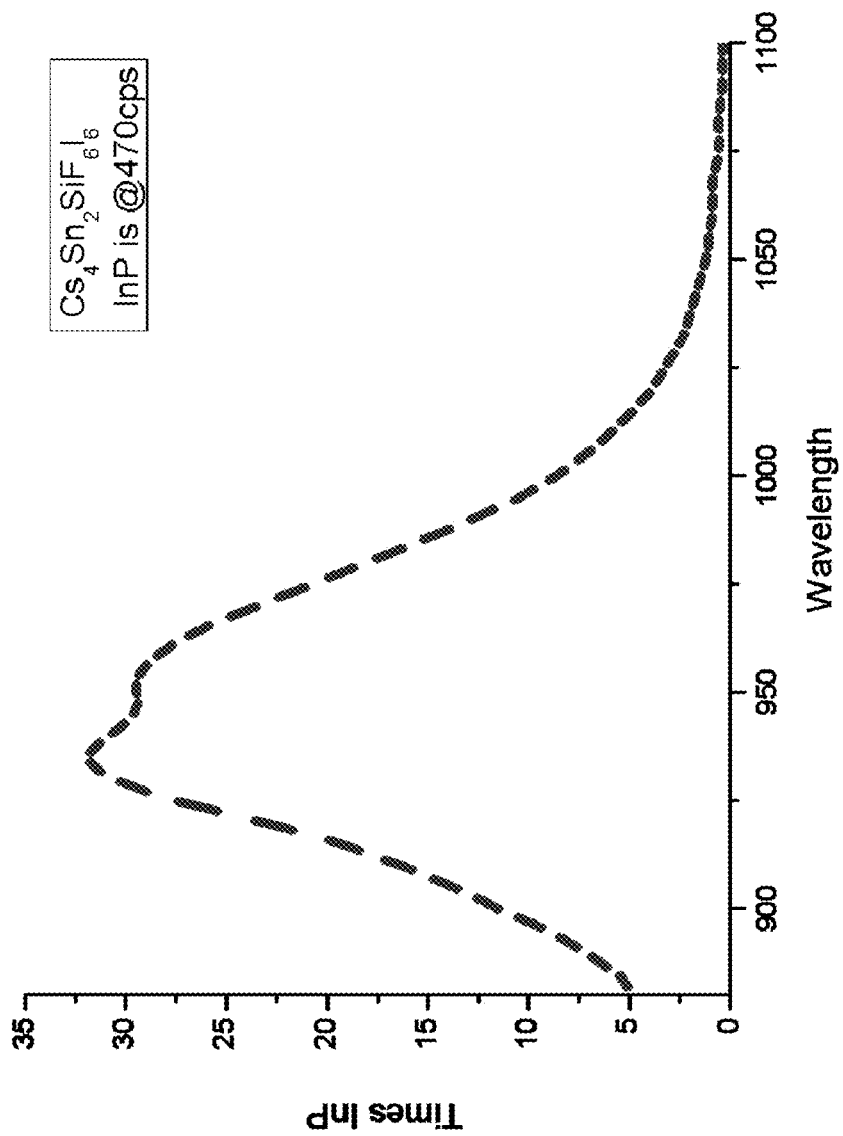
Figure 8C:
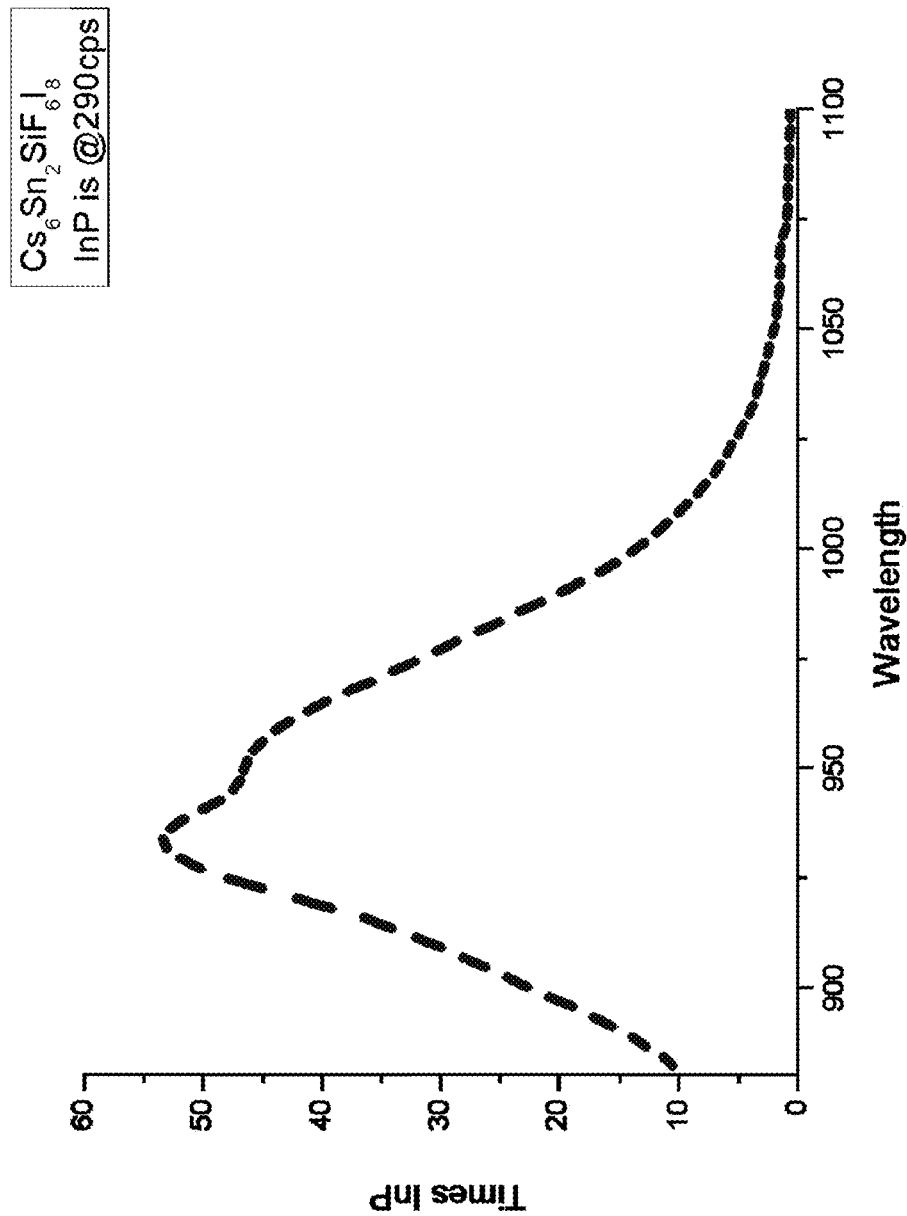

Electrochemical impedance spectroscopy (EIS) was used to characterize the internal resistance and charge transfer kinetics. FIGS. 5 (A), (B), and (C) show the Nyquist plots, Bode phase plots and magnitude of impedance, respectively. The details of EIS analysis are shown in Table 1 with J-V characteristics. F and $SnF_2$ doping reduced the $R_{total}$, giving higher efficiency. The trend in $R_{total}$ is inversely related to the trend in conversion efficiency.

Figure 24:
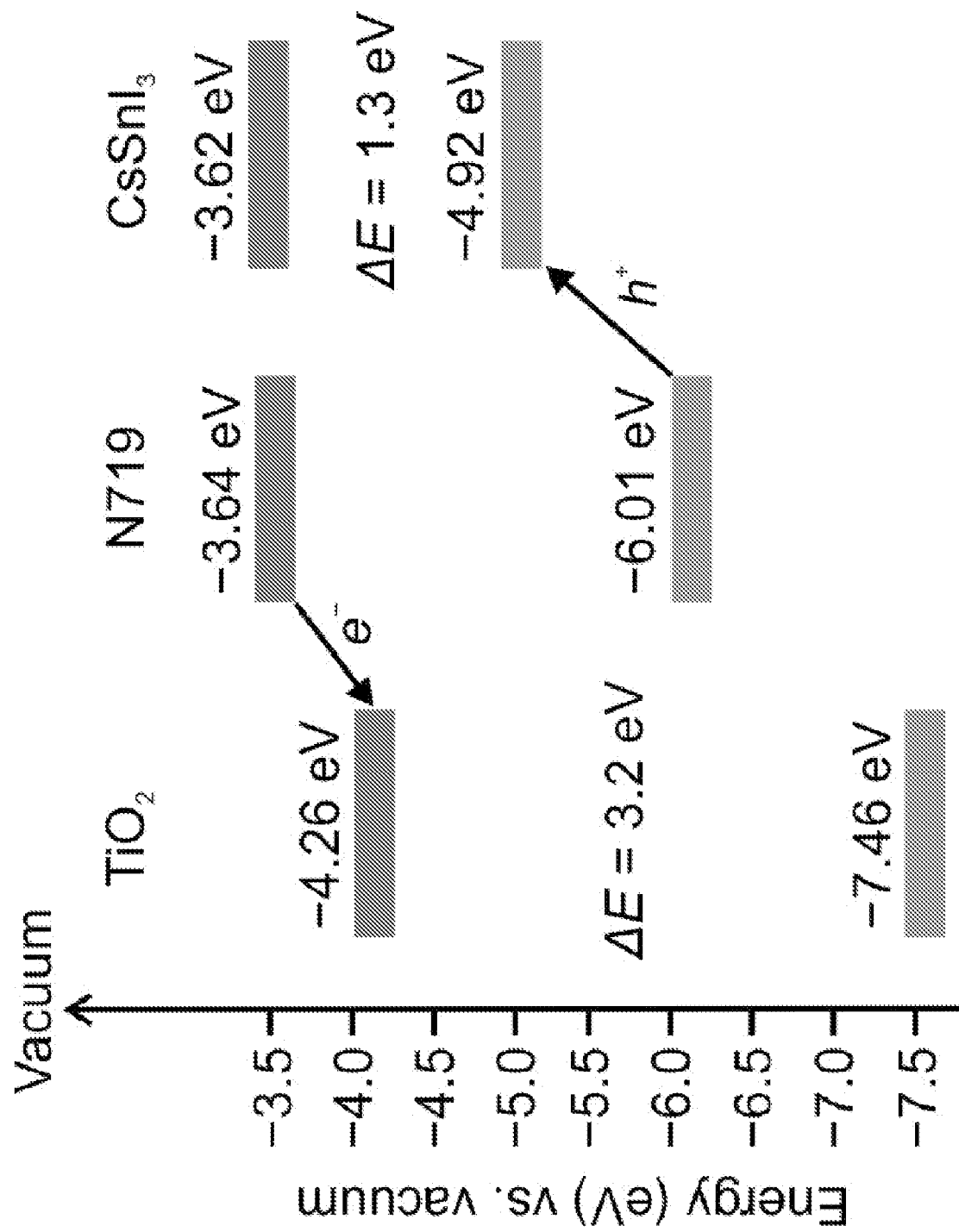
FIG. 24 shows the energy levels of the components of a $CsSnI_3$-based solid-state solar cell. The valence band maximum (lower rectangles) and the conduction band minimum (upper rectangles) of $TiO_2$ and $CsSnI_3$ are represented in eV, along with the energy difference between the edges. The ground (orange) and excited states (blue) of N719 dye is also shown. The energy scale is referenced to the vacuum level.

A schematic diagram of the relative energy levels of $CsSnI_3$, $TiO_2$ and the N719 dye is shown in FIG. 24. The positions of the conduction band minimum (CBM) and the valence band maximum (VBM) of $CsSnI_3$ were aligned by the work function (4.92 eV) according to ultraviolet photoemission spectroscopy study and the energy gap (1.3 eV), relative to those of $TiO_2$ and the N719 dye based on the literature. The diagram validates the fit of $CsSnI_3$ in the present type of solid-state solar cell, giving excellent charge separation and replacing liquid electrolytes. The conduction band minimum lies nearly in the same energy level as the lowest unoccupied molecular orbital (LUMO) of the N719 dye and above the CBM of $TiO_2$. The valence band maximum is positioned above the highest occupied molecular orbital (HOMO) of the dye. Consequently, electrons generated by the dye are transported to the n-type semiconductor $TiO_2$ and the oxidized dye is readily regenerated by the p-type semiconductor $CsSnI_3$ because it a fast hole transporter.

Example 2

This Example provides some illustrative examples of Type I materials and processes for their synthesis. The Type I materials of this example include those comprising two phases, designated categories (A) and (B) in the description that follows.

Type I materials of category (A) have the formula $(Cs_{1+y}SnI_{3+y})_x(MO_y)_{1-x}$: where M=a Group 14 element with y=1 or y=2; or M=a Group 13 or a Group 15 element. The Cs and I content (as CsI) can be varied in these materials to get the optimal photoluminescence intensity. Specific examples include: ($\alpha$) $(Cs_{1+y}SnI_{3+y})_x(MO)_{1-x}$, where M=Si, Ge, Sn, or Pb; and ($\beta$) $(Cs_{1+y}SnI_{3+y})_x(MO_{1.5})_{1-x}$, where M=B, Al, Ga, In, Sc, or Y; ($\gamma$) $(Cs_{1+y}SnI_{3+y})_x(MO_2)_{1-x}$, where M=Si, Ge, Sn, or Pb.

Type I materials of category (B) have the formula $(Cs_{1+y}SnI_{3+y})_x(Cs_xMF_6)_{1-x}$: where M=a Group 15 or a Group 5 element and z=1; or M=a Group 14 or a Group 4 element and z=2; or M=a Group 13 or Group 3 element and z=3. The Cs and I content (as CsI) can be varied to get the optimal photoluminescence intensity. Specific examples include: ($\delta$) $(Cs_{1+y}SnI_{3+y})_{1-x}(CsM_{0.5}F_3)_x$, where M=Si, Ge, Sn, Ti, Zr, or Hf; ($\epsilon$) $(Cs_{1+y}SnI_{3+y})_{1-x}(Cs_{1.5}M_{0.5}F_3)_x$, where M=Al, Ga, In, Sc, or Y; ($\sigma\tau$) $(Cs_{1+y}SnI_{3+y})_{1-x}(Cs_{0.5}M_{0.5}F_3)_x$, where M=P, As, Sb, V, Nb, or Ta.

Sample Synthetic Process 1:

A pyrex ampule was loaded with CsI (1 equivalent) and an amount of $SnI_2$ and SnO as solids. The $SnI_2$/SnO ratio was fixed in such a way that the total Sn content was 1 equivalent. The ampule was sealed under a $10^{-4}$ mbar vacuum and heated up to 450° C. and cooled. The resulting solids were tested for photoluminescence.

Sample Synthetic Process 2:

A pyrex ampule was loaded with $SnI_2$ (1 equivalent) and $MO_X$ (0.5 equiv) and a variable quantity of CsI. The ampule was and heated to 450° C. and cooled. The resulting solids were tested for photoluminescence.

Sample Synthetic Process 3:

A pyrex ampule was loaded with CsI (1 equivalent) and $SnI_2$ and a variable amount of $CsMF_6$. The ampule was heated up to 450° C. and cooled. The resulting solids were tested for photoluminescence.

The PL spectra for the Type I materials are shown in FIGS. 6, 7 and 8(A)-(C).

Example 3

This Example provides some illustrative examples of Type IIA materials and processes for their synthesis. The Type IIA materials of this example include those comprising the phase designated (C) in the description that follows.

The phase of type (C) has the formula $AMI_3$: where A=methylammonium ($CH_3NH_3^+$), formamidinium (HC$(NH_2)_2^+$), methylformamidinium ($H_3CC(NH_2)_2^+$) or guanidinium ($C(NH_2)_3^+$). The structural formulae of these organic cations is shown in Chart 1.

Chart 1. Structural formulae of the organic cations discussed in this chapter.

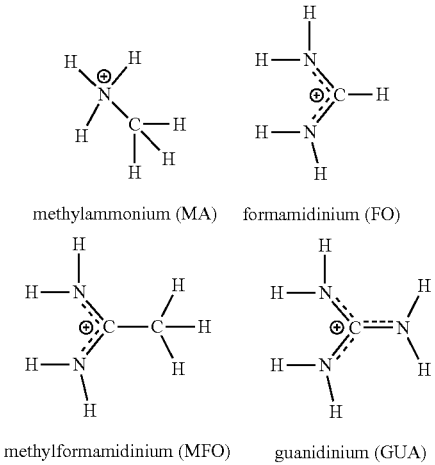

methylammonium (MA)   formamidinium (FO)

methylformamidinium (MFO)   guanidinium (GUA)

Specific examples include: (ζ) $CH_3NH_3MI_3$, where M=Ge, Sn, or Pb; (η)$HC(NH_2)_2MI_3$, where M=Ge, Sn, or Pb; (θ)$H_3CC(NH_2)_2MI_3$, where M=Ge, Sn, or Pb; and (ι) $C(NH_2)_3MI_3$, where or M=Ge, Sn, Pb.

Figure 9:
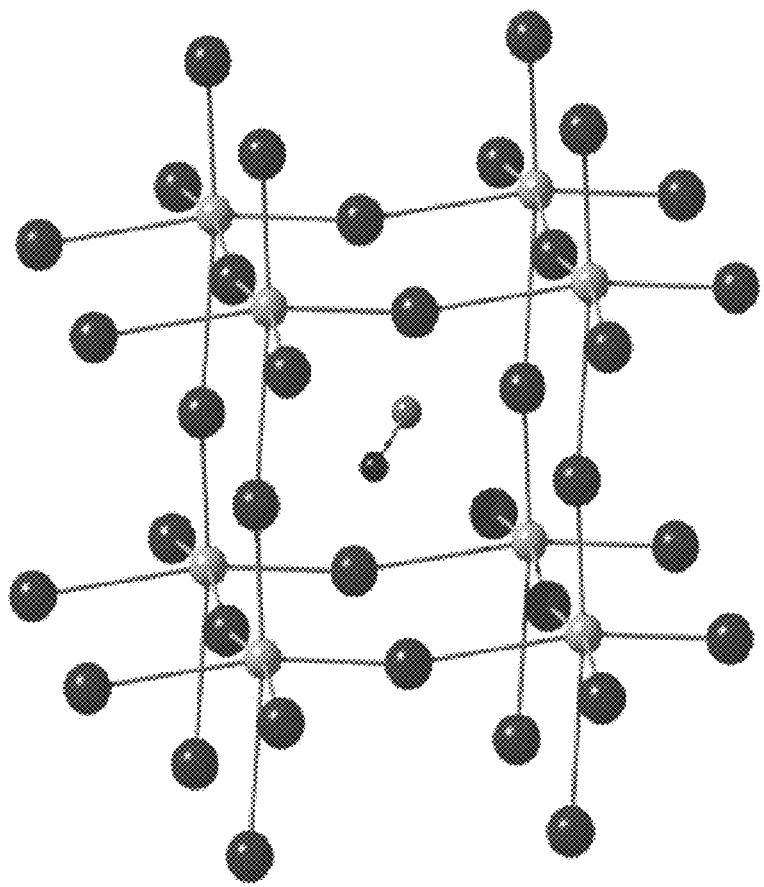
FIG. 9 shows a portion of the crystal structure of Type IIA material $CH_3NH_3GeI_3$ highlighting the perovskite building block. Color code. Ge: mid-size, light gray; I: large, dark; N: small, dark; C: small, gray.

FIG. 9 shows a portion of the crystal structure of Type IIA material $CH_3NH_3GeI_3$ highlighting the perovskite building block.

Table 3 provides atomic coordinates ($\times 10^4$) and equivalent isotropic displacement parameters ($E^2 \times 10^3$) for the $CH_3NH_3GeI_3$. U(eq) is defined as one third of the trace of the orthogonalized $U^{ji}$ tensor.

TABLE 3

|    | x       | y       | z       | U(eq)   |
|----|---------|---------|---------|---------|
| Ge | 6667    | 3333    | 315(5)  | 29(1)   |
| I  | 5050(1) | 4950(1) | 1568(6) | 57(1)   |
| C  | 6667    | 3333    | 5580(90)| 130(30) |
| N  | 6667    | 3333    | 4400(200)| 370(110)|

Figure 10:
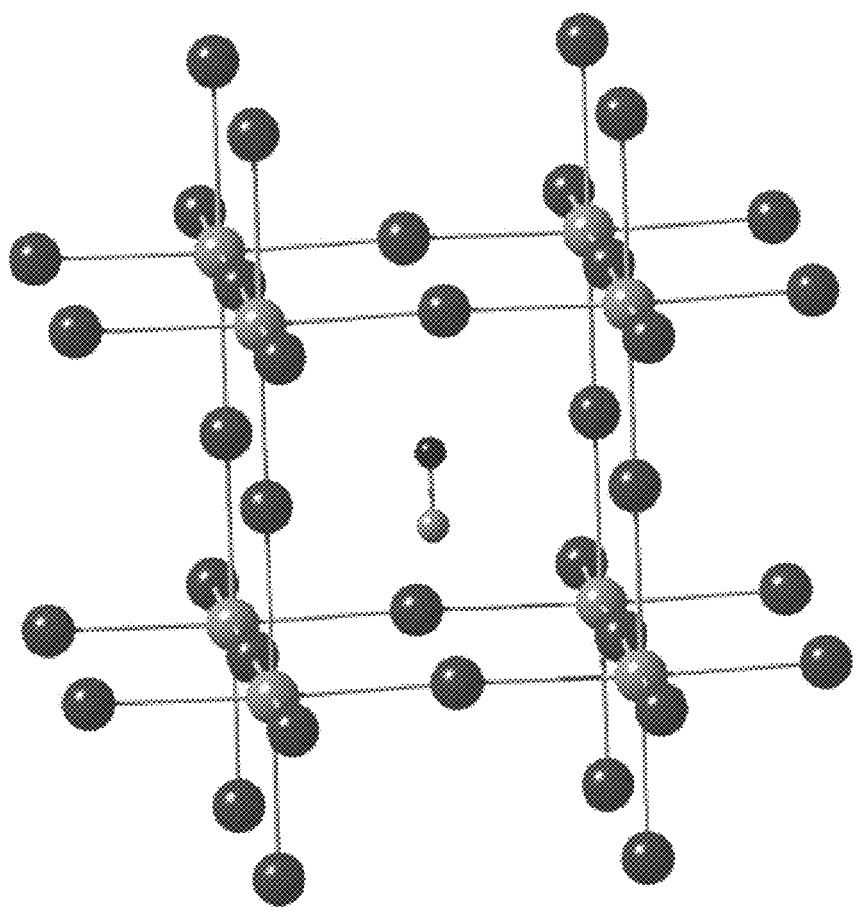
FIG. 10 shows a portion of the crystal structure of $CH_3NH_3SnI_3$ highlighting the perovskite building block. Color code. Sn: large, gray; I: large, dark; N: small, dark; C: small, gray.

FIG. 10 shows a portion of the crystal structure of $CH_3NH_3SnI_3$ highlighting the perovskite building block.

Table 4 provides crystal data structure refinement for the $CH_3NH_3SnI_3$.

TABLE 4

| Empirical formula | CH6I3NSn |
|---|---|
| Formula weight | 531.46 |
| Temperature | 293(2) K |
| Wavelength | 0.71073 E |
| Crystal system | Tetragonal |
| Space group | P4mm |
| Unit cell dimensions | a = 6.2302(9) E    α = 90°. |
|  | b = 6.2302(9) E    β = 90°. |
|  | c = 6.2316(12) E   γ = 90°. |
| Volume | 241.88(7) $E^3$ |
| Z | 1 |
| Density (calculated) | 3.649 $Mg/m^3$ |
| Absorption coefficient | 12.128 $mm^{-1}$ |
| F(000) | 228 |
| Theta range for data collection | 3.27 to 24.78°. |
| Index ranges | -7 <= h <= 7, -7 <= k <= 7, |
|  | -7 <= l <= 7 |
| Reflections collected | 1520 |
| Independent reflections | 294 [R(int) = 0.0331] |
| Completeness to theta = 24.78° | 98.2% |
| Refinement method | Full-matrix least-squares on $F^2$ |
| Data/restraints/parameters | 294/1/18 |
| Goodness-of-fit on $F^2$ | 0.794 |
| Final R indices [I > 2sigma(I)] | R1 = 0.0239, wR2 = 0.0839 |
| R indices (all data) | R1 = 0.0323, wR2 = 0.0984 |
| Absolute structure parameter | 0.6(5) |
| Largest diff. peak and hole | 0.574 and −0.538 e · $E^{-3}$ |

Table 5 provides atomic coordinates ($\times 10^4$) and equivalent isotropic displacement parameters ($E^2 \times 10^3$) for the $CH_3NH_3SnI_3$. U(eq) is defined as one third of the trace of the orthogonalized $U^{ji}$ tensor.

TABLE 5

|      | x     | y    | z        | U(eq)   |
|------|-------|------|----------|---------|
| Sn   | 0     | 0    | 9484     | 28(1)   |
| I(1) | -5000 | 0    | 9582(15) | 84(1)   |
| I(2) | 0     | 0    | 14608(10)| 85(2)   |
| N    | 5000  | 5000 | 4800(200)| 150(40) |
| C    | 5000  | 5000 | 2840(90) | 160(50) |

Figure 11:
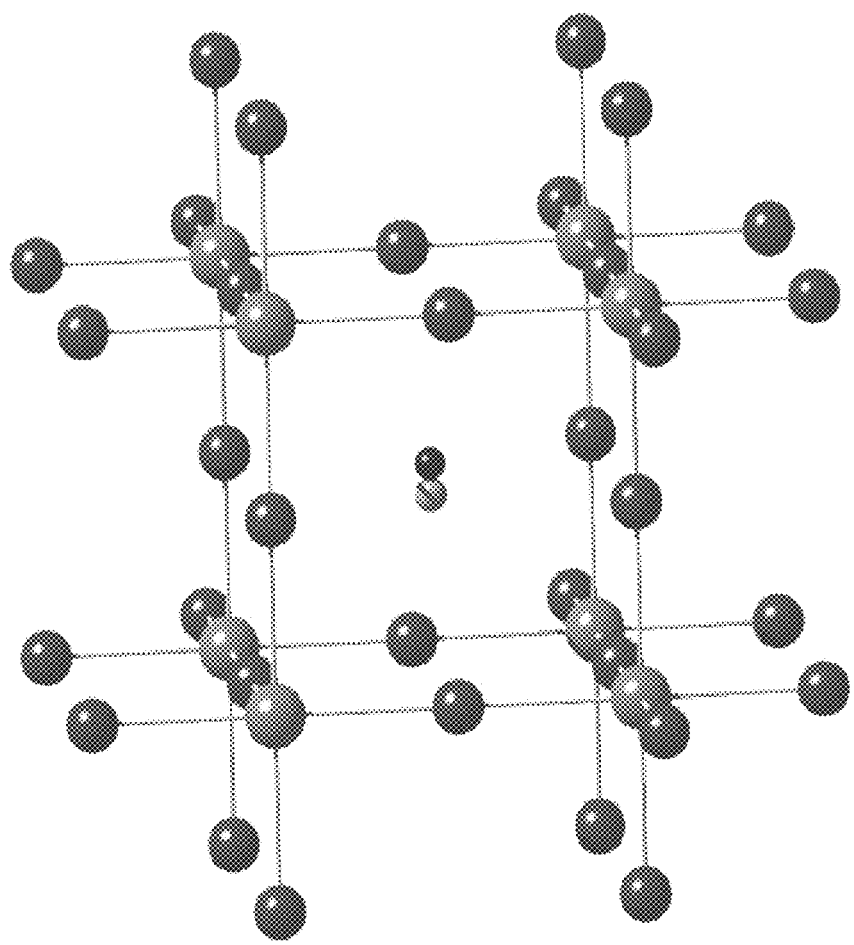
FIG. 11 shows a portion of the crystal structure of $CH_3NH_3PbI_3$ highlighting the perovskite building block. Color code. Pb: large, gray; I: large, dark; N: small, dark; C: small, gray.

FIG. 11 shows a portion of the crystal structure of $CH_3NH_3PbI_3$ highlighting the perovskite building block.

Table 6 provides crystal data structure refinement for the $CH_3NH_3PbI_3$.

TABLE 6

| Empirical formula | CH6I3NPb |
|---|---|
| Formula weight | 619.96 |
| Temperature | 293(2) K |
| Wavelength | 0.71073 E |
| Crystal system | Tetragonal |
| Space group | P4mm |
| Unit cell dimensions | a = 6.2641(9) E    α = 90°. |
|  | b = 6.2641(9) E    β = 90°. |
|  | c = 6.3242(13) E   γ = 90°. |
| Volume | 248.15(7) $E^3$ |
| Z | 1 |
| Density (calculated) | 4.148 $Mg/m^3$ |
| Absorption coefficient | 26.244 $mm^{-1}$ |
| F(000) | 260 |
| Theta range for data collection | 3.25 to 24.96°. |
| Index ranges | -7 <= h <= 7, -7 <= k <= 7, |
|  | -7 <= l <= 6 |
| Reflections collected | 1543 |
| Independent reflections | 275 [R(int) = 0.0316] |
| Completeness to theta = 24.96° | 95.1% |
| Refinement method | Full-matrix least-squares on $F^2$ |
| Data/restraints/parameters | 275/1/15 |
| Goodness-of-fit on $F^2$ | 1.717 |

TABLE 6-continued

| | |
|---|---|
| Final R indices [I > 2sigma(I)] | R1 = 0.0631, wR2 = 0.1859 |
| R indices (all data) | R1 = 0.0650, wR2 = 0.1871 |
| Absolute structure parameter | 0.6(6) |
| Largest diff. peak and hole | 5.168 and −5.446 e · E$^{-3}$ |

Table 7 provides atomic coordinates (×10$^4$) and equivalent isotropic displacement parameters (E$^2$×10$^3$) for the CH$_3$NH$_3$PbI$_3$. U(eq) is defined as one third of the trace of the orthogonalized U$^{ji}$ tensor.

TABLE 7

| | x | y | z | U(eq) |
|---|---|---|---|---|
| Pb(1) | 5000 | 5000 | 2547 | 26(1) |
| I(3) | 0 | 5000 | 2550(40) | 177(5) |
| I(2) | 5000 | 5000 | 7550(30) | 82(2) |
| C(2) | 0 | 0 | 8000(3000) | 600(800) |
| N(10) | 0 | 0 | 7200(1900) | 100(600) |

Sample Synthetic Process 4:

A solution mixture of concentrated HI/H$_3$PO$_2$ (4/1 v/v) was prepared. Addition of SnI$_2$ (1 equivalent) provided a clear solution which was maintained at 120° C. Subsequent addition of the corresponding organic iodide (1 equivalent), precipitated the desired material.

Example 4

This Example provides some illustrative examples of Type IIB materials and processes for their synthesis. The Type IIB materials of this example include those comprising the phase designated (D) in the description that follows.

The phase of type (D) has the formula ASn$_x$I$_y$: where A=alkyl viologen (RV, R=H, Me, Et, etc.) or a polyaromatic pyridine. The structural formulae of these organic cations is shown in Chart 2.

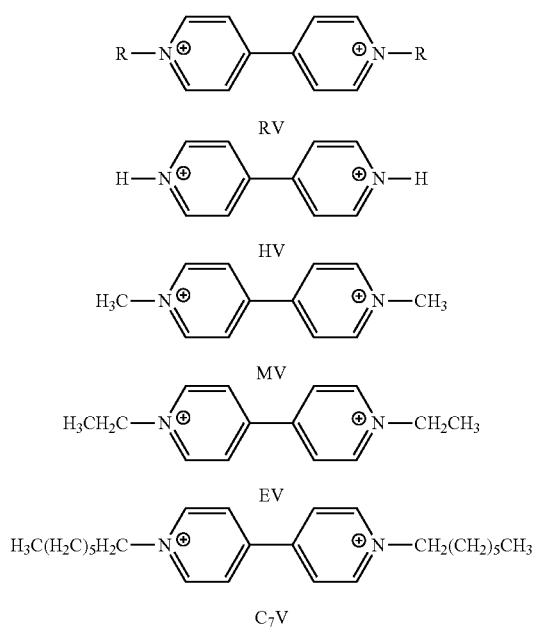

Chart 2. Selected structural formulae of alkyl viologens.

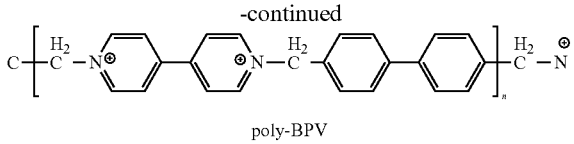

poly-BPV

Specific examples include: (K) HVSnI$_4$ and RVSn$_2$I$_6$, where R=methyl, ethyl, heptyl, etc. . . . ) and polymeric viologens; and (2) AcrSnI$_3$ and ASnI$_3$ materials, where A is a polyaromatic pyridine.

Figure 12:
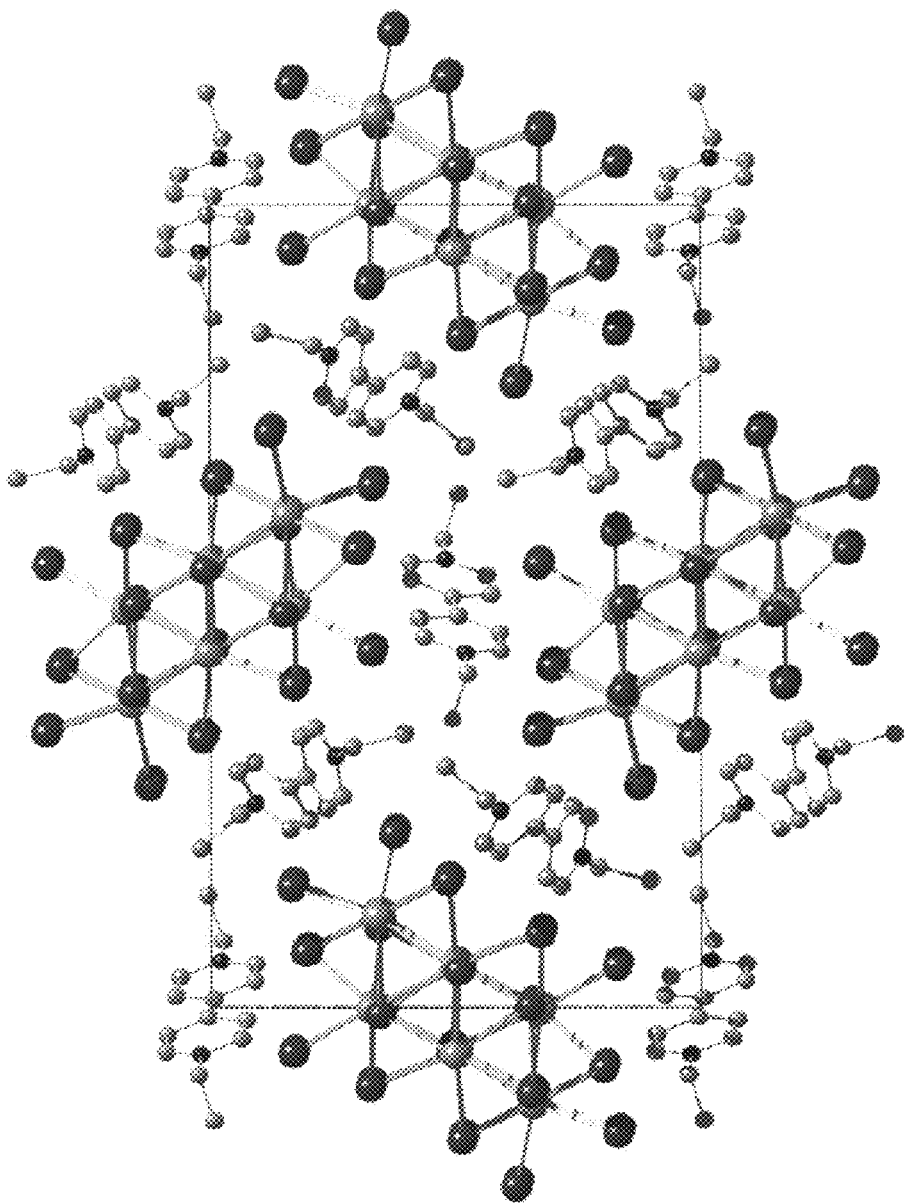
FIG. 12 shows the unit cell of $EVSn_2I_6$ viewing along the 1-dimensional $Sn_2I_6^{2-}$ chains. Color code. Sn: large, gray; I: large, dark; N: small, dark; C: small, gray.

FIG. 12 shows the unit cell of EVSn$_2$I$_6$ viewing along the 1-dimensional Sn$_2$I$_6^{2-}$ chains.

Table 8 provides crystal data structure refinement for the of EVSn$_2$I$_6$.

TABLE 8

| | |
|---|---|
| Empirical formula | C14I6N2Sn2 |
| Formula weight | 1194.94 |
| Temperature | 293(2) K |
| Wavelength | 0.71073 E |
| Crystal system | Monoclinic |
| Space group | P2$_1$/c |
| Unit cell dimensions | a = 12.116(2) E  α = 90°. |
| | b = 13.941(3) E  β = 90.51(3)°. |
| | c = 24.677(5) E  γ = 90°. |
| Volume | 4167.8(14) E$^3$ |
| Z | 6 |
| Density (calculated) | 2.857 Mg/m$^3$ |
| Absorption coefficient | 8.465 mm$^{-1}$ |
| F(000) | 3096 |
| Theta range for data collection | 1.65 to 25.00°. |
| Index ranges | −14 <= h <= 14, −16 <= k <= 16, −29 <= l <= 29 |
| Reflections collected | 26382 |
| Independent reflections | 7347 [R(int) = 0.1134] |
| Completeness to theta = 25.00° | 100.0% |
| Refinement method | Full-matrix least-squares on F$^2$ |
| Data/restraints/parameters | 7347/0/325 |
| Goodness-of-fit on F$^2$ | 0.928 |
| Final R indices [I > 2sigma(I)] | R1 = 0.0626, wR2 = 0.0733 |
| R indices (all data) | R1 = 0.1489, wR2 = 0.0896 |
| Largest diff. peak and hole | 0.845 and −1.153 e · E$^{-3}$ |

Table 9 provides atomic coordinates (×10$^4$) and equivalent isotropic displacement parameters (E$^2$×10$^3$) for the EVSn$_2$I$_6$. U(eq) is defined as one third of the trace of the orthogonalized U$^{ji}$ tensor.

TABLE 9

| | x | y | z | U(eq) |
|---|---|---|---|---|
| I(72) | 8381(1) | 3448(1) | 1032(1) | 57(1) |
| Sn(2) | 6690(1) | 4993(1) | 543(1) | 44(1) |
| I(3) | 15001(1) | 13469(1) | −48(1) | 52(1) |
| I(4) | 8300(1) | 80(1) | 4496(1) | 53(1) |
| Sn(5) | 9950(1) | 6716(1) | −16(1) | 50(1) |
| Sn(6) | 3403(1) | 3423(1) | 1174(1) | 58(1) |
| I(8) | 8102(1) | 6733(1) | 946(1) | 59(1) |
| I(9) | 8543(1) | 8026(1) | −735(1) | 64(1) |
| I(10) | 4536(1) | 1677(1) | 1536(1) | 91(1) |
| I(11) | 11097(1) | 8305(1) | 539(1) | 81(1) |
| I(12) | 2292(1) | 3768(1) | 2202(1) | 88(1) |
| C(2) | 7783(11) | 1974(10) | 2886(6) | 44(4) |
| C(3) | 4537(12) | 2867(14) | 3261(10) | 101(8) |
| N(4) | 10994(10) | 918(13) | 2549(7) | 72(4) |
| C(9) | 4559(17) | 3953(17) | 3417(12) | 120(9) |
| C(13) | 12153(13) | 623(19) | 2424(9) | 108(8) |
| C(15) | 14412(10) | 9952(13) | −123(6) | 53(4) |
| C(19) | 12081(12) | −199(16) | 2004(11) | 108(8) |
| C(20) | 8916(11) | 1589(12) | 2763(6) | 50(4) |
| N(22) | 12369(10) | 9799(11) | −572(6) | 65(4) |
| C(26) | 7119(14) | 2404(14) | 2482(7) | 78(6) |
| C(27) | 14059(13) | 9072(11) | −331(8) | 71(6) |

TABLE 9-continued

| | x | y | z | U(eq) |
|---|---|---|---|---|
| C(30) | 6335(15) | 2134(13) | 3515(7) | 72(5) |
| N(31) | 5692(10) | 2555(10) | 3128(7) | 64(4) |
| C(34) | 7391(12) | 1840(14) | 3403(6) | 64(5) |
| C(36) | 10461(13) | 533(14) | 2954(6) | 63(5) |
| I(40) | 5331(1) | 4855(1) | 1609(1) | 64(1) |
| C(47) | 12989(13) | 9044(14) | −555(9) | 81(6) |
| C(49) | 12674(15) | 10652(13) | −376(8) | 72(5) |
| C(61) | 11205(11) | 9720(15) | −812(8) | 79(6) |
| C(66) | 6073(14) | 2688(16) | 2628(9) | 83(7) |
| C(70) | 11262(14) | 10040(20) | −1384(10) | 117(9) |
| C(74) | 9403(12) | 852(13) | 3067(6) | 62(5) |
| C(8) | 9515(15) | 2016(16) | 2329(7) | 91(7) |
| C(18) | 10576(16) | 1623(16) | 2235(8) | 85(6) |
| C(12) | 13746(14) | 10770(13) | −136(9) | 85(6) |

Figure 13:
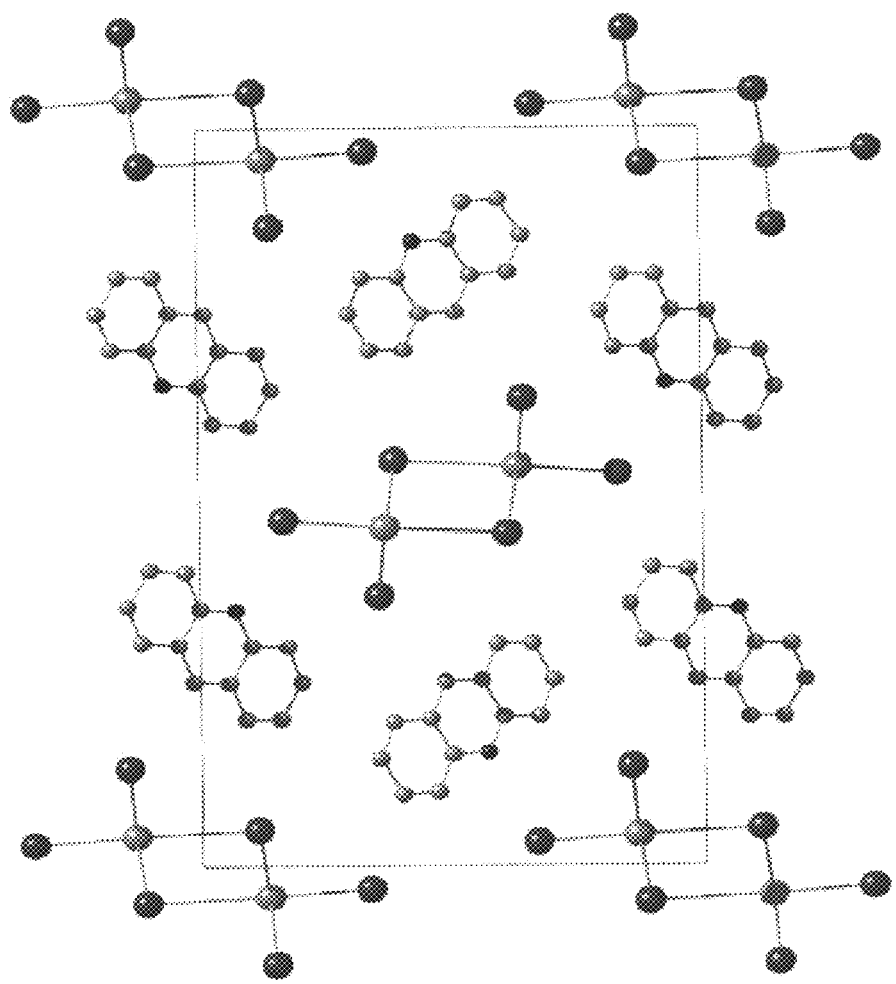
FIG. 13 shows the unit cell of $AcrSnI_3$ viewing along the 1-dimensional $SnI_3^-$ chains. Color code. Sn: large, gray; I: large, dark; N: small, dark; C: small, gray.

FIG. 13 shows the unit cell of AcrSnI$_3$ viewing along the 1-dimensional SnI$_3^-$ chains.

Table 10 provides crystal data structure refinement for the of AcrSnI$_3$.

TABLE 10

| | |
|---|---|
| Empirical formula | C13H10I3NSn |
| Formula weight | 679.61 |
| Temperature | 293(2) K |
| Wavelength | 0.71073 E |
| Crystal system | Monoclinic |
| Space group | P2$_1$/n |
| Unit cell dimensions | a = 4.6467(9) E  α = 90°. |
| | b = 24.710(5) E  β = 90.18(3)°. |
| | c = 14.817(3) E  γ = 90°. |
| Volume | 1701.2(6) E$^3$ |
| Z | 4 |
| Density (calculated) | 2.653 Mg/m$^3$ |
| Absorption coefficient | 6.930 mm$^{-1}$ |
| F(000) | 1216 |
| Theta range for data collection | 1.60 to 24.99°. |
| Index ranges | −5 <= h <= 5, −29 <= k <= 29, −17 <= l <= 17 |
| Reflections collected | 12633 |
| Independent reflections | 2956 [R(int) = 0.0548] |
| Completeness to theta = 24.99° | 98.1% |
| Refinement method | Full-matrix least-squares on F$^2$ |
| Data/restraints/parameters | 2956/0/164 |
| Goodness-of-fit on F$^2$ | 1.088 |
| Final R indices [I > 2sigma(I)] | R1 = 0.0483, wR2 = 0.0896 |
| R indices (all data) | R1 = 0.0636, wR2 = 0.0989 |
| Largest diff. peak and hole | 1.311 and −1.427 e · E$^{-3}$ |

Table 11 provides atomic coordinates (×10$^4$) and equivalent isotropic displacement parameters (E$^2$×10$^3$) for the AcrSnI$_3$. U(eq) is defined as one third of the trace of the orthogonalized U$^{ji}$ tensor.

TABLE 11

| | x | y | z | U(eq) |
|---|---|---|---|---|
| I(1) | 2328(3) | 1337(1) | 1439(1) | 56(1) |
| Sn(2) | 7159(3) | 413(1) | 1325(1) | 49(1) |
| I(2) | 2383(3) | −493(1) | 1123(1) | 59(1) |
| I(3) | 6881(3) | 315(1) | 3333(1) | 58(1) |
| C(1) | −2270(40) | −2498(5) | 4865(8) | 52(4) |
| C(2) | −4220(40) | −2514(5) | 5577(10) | 54(4) |
| C(3) | −1990(40) | −1508(5) | 4997(8) | 50(4) |
| N(1) | −3840(30) | −1535(4) | 5707(8) | 52(3) |
| C(4) | 1890(40) | −1456(7) | 3552(10) | 76(5) |
| C(5) | −880(40) | −1003(6) | 4713(11) | 56(4) |
| C(6) | 990(40) | −1954(8) | 3827(11) | 77(6) |
| C(7) | −1150(40) | −1995(6) | 4567(9) | 55(4) |
| C(8) | 1050(40) | −967(7) | 3993(12) | 71(5) |
| C(9) | −470(40) | −1994(6) | 894(10) | 52(4) |
| C(10) | 8260(50) | 2511(7) | 2998(10) | 70(5) |
| C(11) | 7160(40) | 2024(5) | 3270(8) | 56(4) |

TABLE 11-continued

| | x | y | z | U(eq) |
|---|---|---|---|---|
| C(12) | 5100(30) | 2016(5) | 3991(9) | 45(3) |
| C(13) | −2480(50) | −1992(5) | 1582(10) | 72(5) |

Sample Synthetic Process 5:

A solution mixture of concentrated HI/H$_3$PO$_2$ (4/1 v/v) was prepared. Addition of SnI$_2$ (1 equivalent) provided a clear solution which was maintained at 120° C. Subsequent addition of the corresponding organic iodide (1 equivalent), precipitated the desired material.

Figures 14A, 14B:
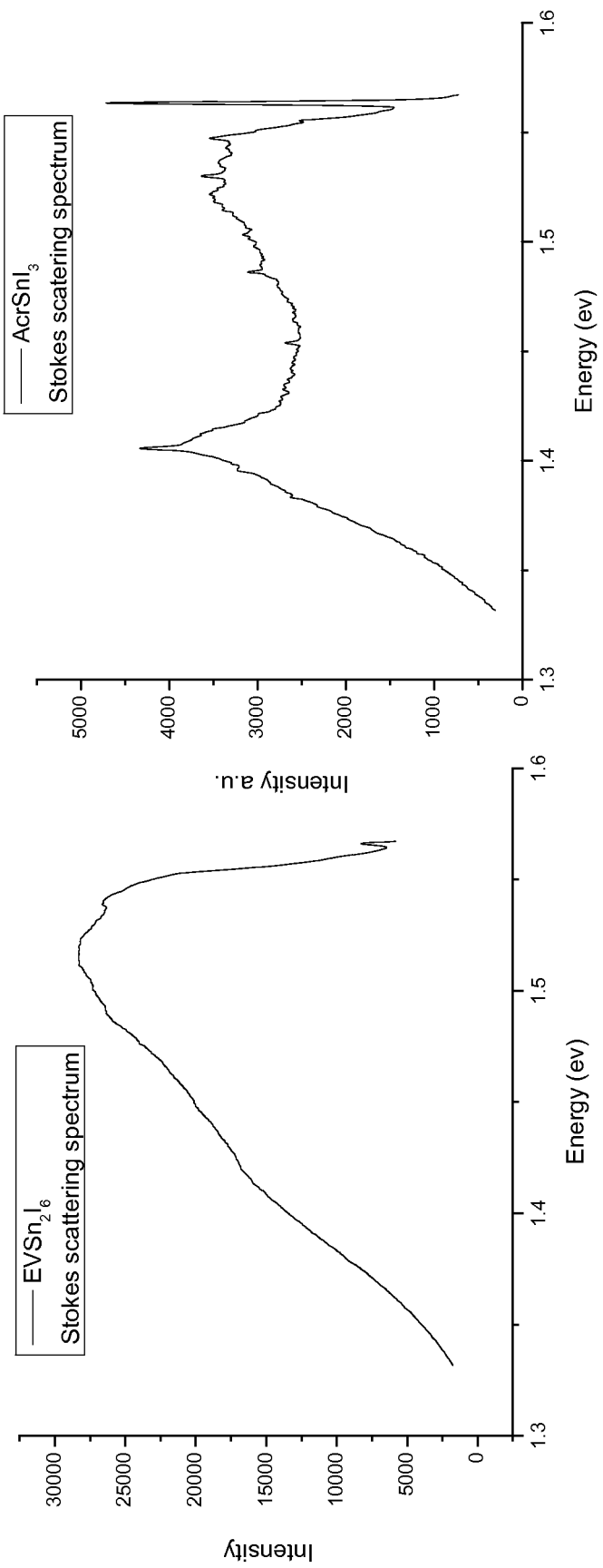
FIG. 14 shows the PL emission vs. energy data for (A) $EVSn_2I_6$ and (B) $AcrSnI_3$.

FIG. 14 shows the PL emission vs. energy data for Type IIB materials on 785 nm (1.58 eV) excitation as measured using a Raman scattering setup. (Note, the above-described Type IIA and Type IIB materials are parent phases for the Type III materials described below. Therefore, PL data for the Type IIA materials are included in the description of Type III materials as well.)

Example 5

This Example provides some illustrative examples of Type III materials and processes for their synthesis. The Type III materials of this example include those comprising the phase designated (E) in the description that follows.

The phase of type (E) has the formula AMIX$_2$: where, in some embodiments, A=Cs, methylammonium (CH$_3$NH$_3^+$), formamidinium (HC(NH$_2$)$_2^+$), methylformamidinium (H$_3$CC(NH$_2$)$_2^+$) or guanidinium (C(NH$_2$)$_3^+$), M=a Group 14 element and X=a Group 17 element. Specific examples include: (µ) CsMIX$_2$, where M=Ge, Sn, or Pb and X can be any combination of halides; (ν) CH$_3$NH$_3$MIX$_2$, where M=Ge, Sn, or Pb and X can be any combination of halides; (ξ) HC(NH$_2$)$_2$MIX$_2$, where M=Ge, Sn, or Pb and X can be any combination of halides; (o) H$_3$CC(NH$_2$)$_2$MIX$_2$, where M=Ge, Sn, or Pb and X can be any combination of halides; and (π) C(NH$_2$)$_3$MIX$_2$, where M=Ge, Sn, or Pb and X can be any combination of halides.

Figure 15:
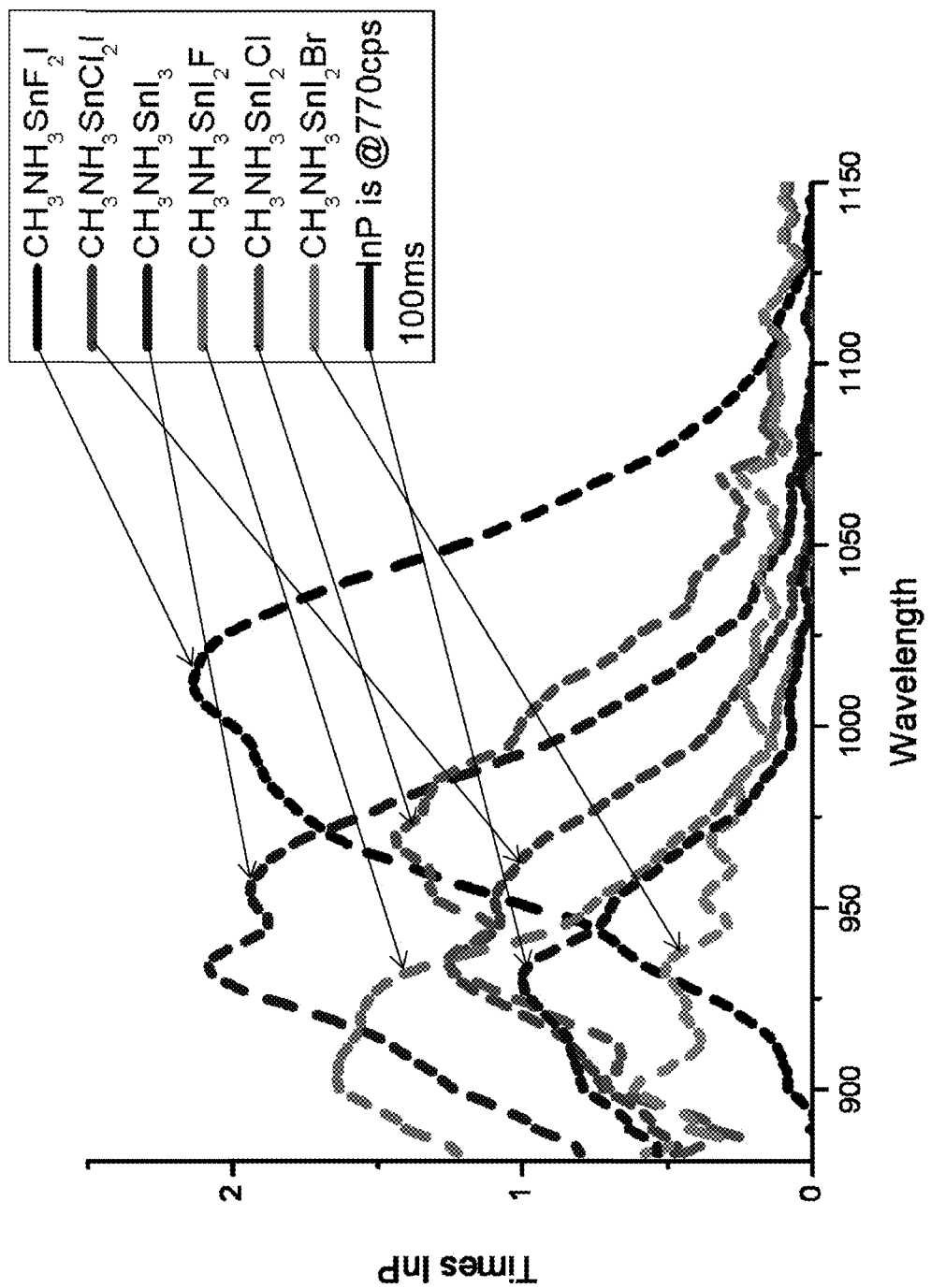
FIG. 15 shows the PL emission vs. wavelength data for $CH_3NH_3SnIX_2$ phases.

FIG. 15 shows the PL emission vs. wavelength data for CH$_3$NH$_3$SnIX$_2$ phases.

Sample Synthetic Process 6:

A pyrex ampule was loaded with CH$_3$NH$_3$X or HC(NH$_2$)$_2$X (1 equivalent), SnX$_2$ or PbX$_2$ or mixtures of them (1 equivalent), where X is a Group 17 element, to achieve the corresponding X/I ratio. The ampule was heated up to 350° C. and cooled. The resulting solids were tested for photoluminescence.

Figure 16:
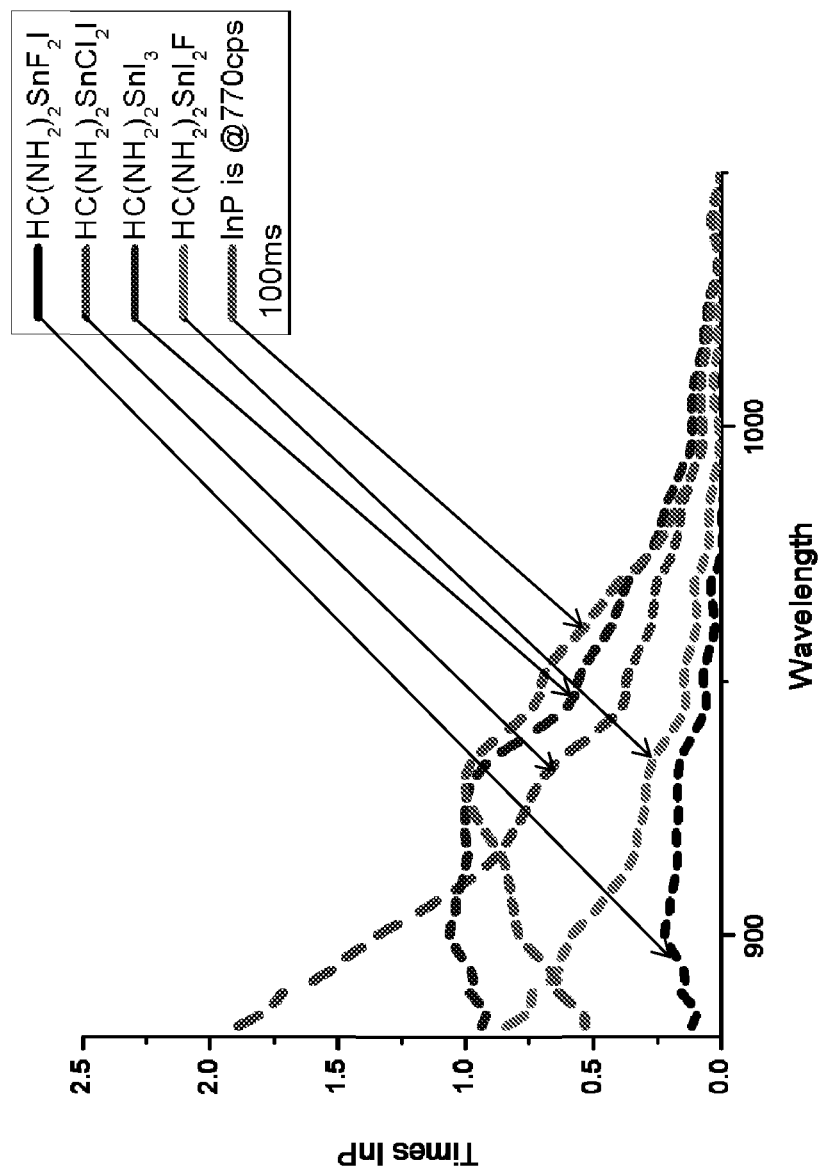
FIG. 16 shows the PL emission vs. wavelength spectra for $HC(NH_2)_2SnIX_2$ phases at a first emission wavelength range.

FIG. 16 shows PL emission vs. wavelength for HC(NH$_2$)$_2$SnIX$_2$ phases for the first emission wavelength.

Figure 17:
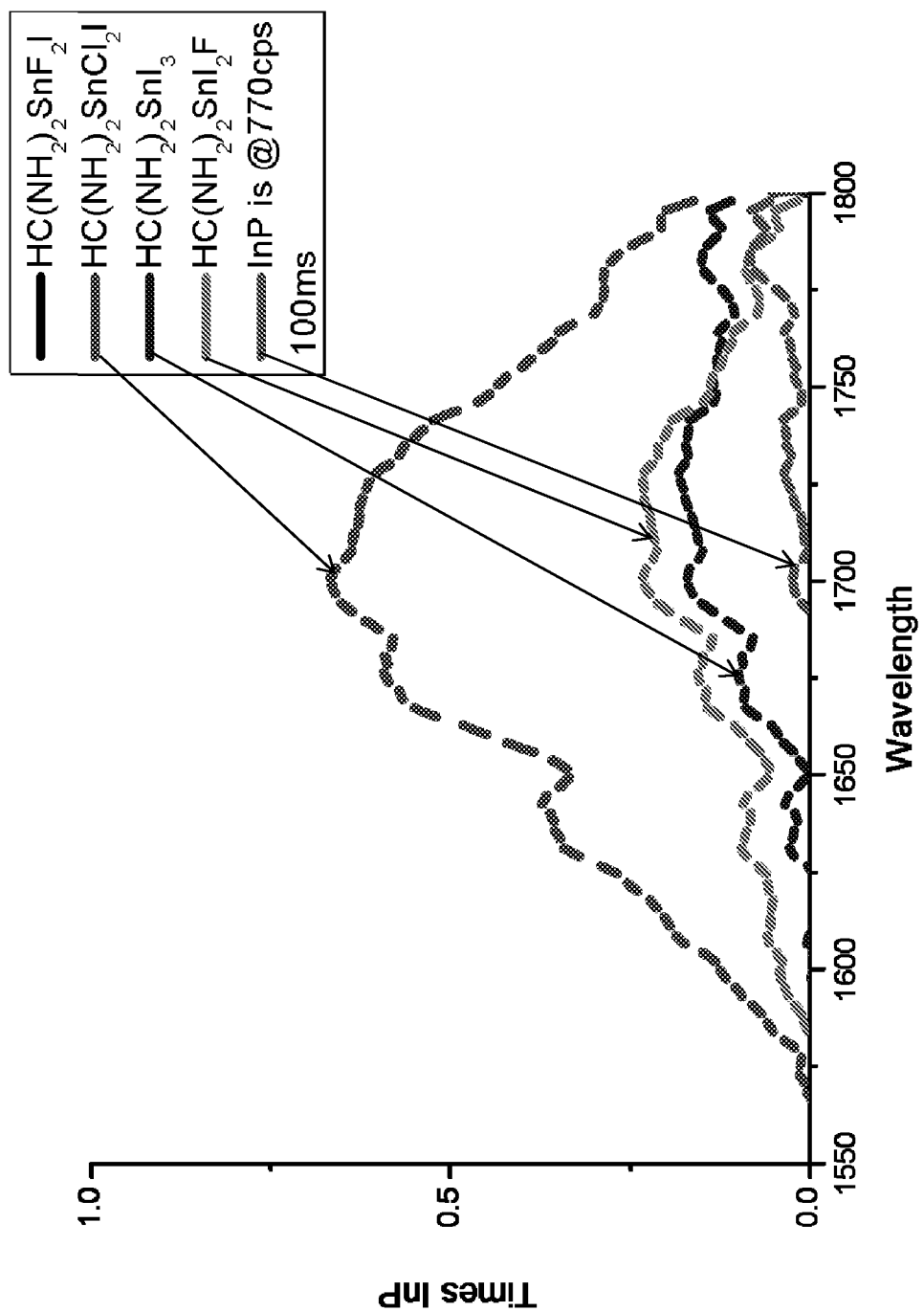
FIG. 17 shows the PL emission vs. wavelength spectra for $HC(NH_2)_2SnIX_2$ phases at a second emission wavelength range.

FIG. 17 shows PL emission vs. wavelength for HC(NH$_2$)$_2$SnIX$_2$ phases for the second emission wavelength.

Figure 18:
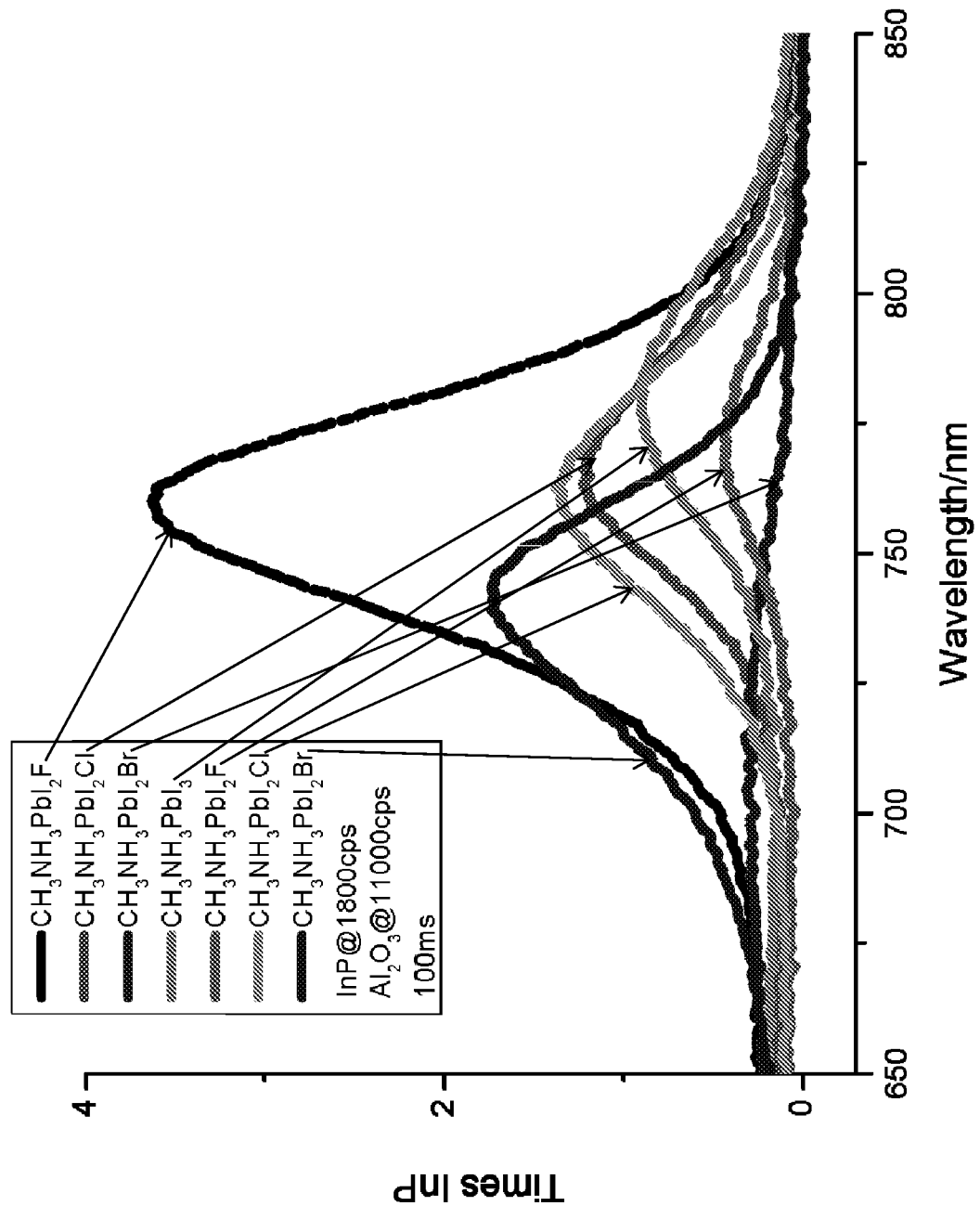
FIG. 18 shows the PL emission vs. wavelength spectra for $CH_3NH_3PbIX_2$ phases at a first emission wavelength range.

FIG. 18 shows PL emission vs. wavelength for CH$_3$NH$_3$PbIX$_2$ phases for the first emission wavelength.

Figure 19:
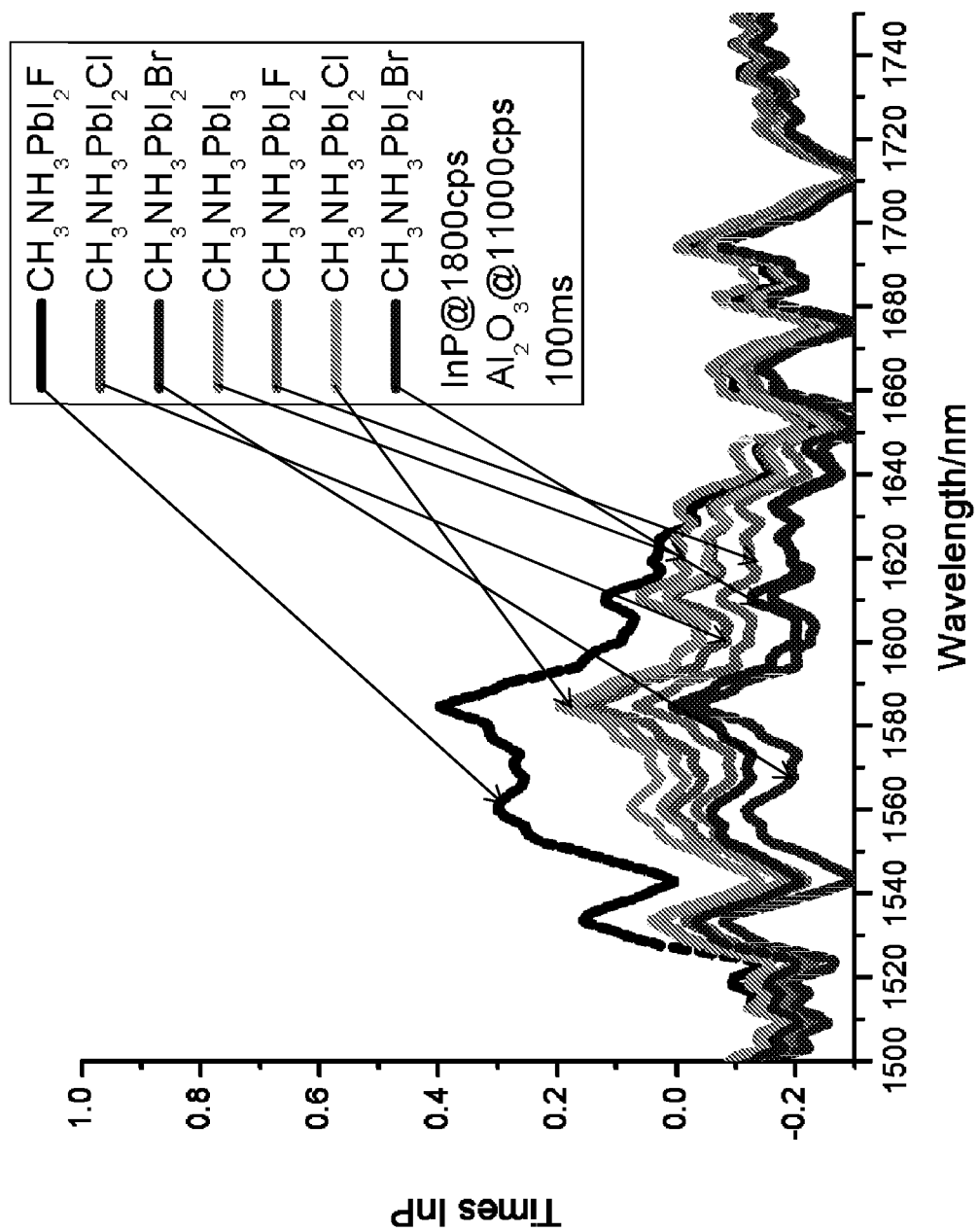
FIG. 19 shows the PL emission vs. wavelength spectra for $CH_3NH_3PbIX_2$ phases at a second wavelength range.

FIG. 19 shows PL emission vs. wavelength for CH$_3$NH$_3$PbIX$_2$ phases for the second emission wavelength.

Sample Synthetic Process 7:

CH$_3$NH$_3$I or HC(NH$_2$)$_2$I (1 equivalent), SnI$_2$ or PbI$_2$ or mixtures of them (1 equivalent), where X is a group 17 element, were ground finely at room temperature. The resulting solids were then tested for photoluminescence.

Example 6

This Example provides some illustrative examples of Type IV materials and processes for their synthesis. The Type IV materials of this example include those comprising the phase designated (F) in the description that follows.

The phase of type (F) includes germanium iodides having the formulas: $GeI_2$, $GeI_4$, $AGeI_5$ and $A_2GeI_6$, where A is a Group 1 metal or an organic cation. Specific examples include: (ρ) $GeI_1$ and $GeI4$; (σ) $AGeI_5$; and (τ) $A_2GeI_6$.

Figure 20:
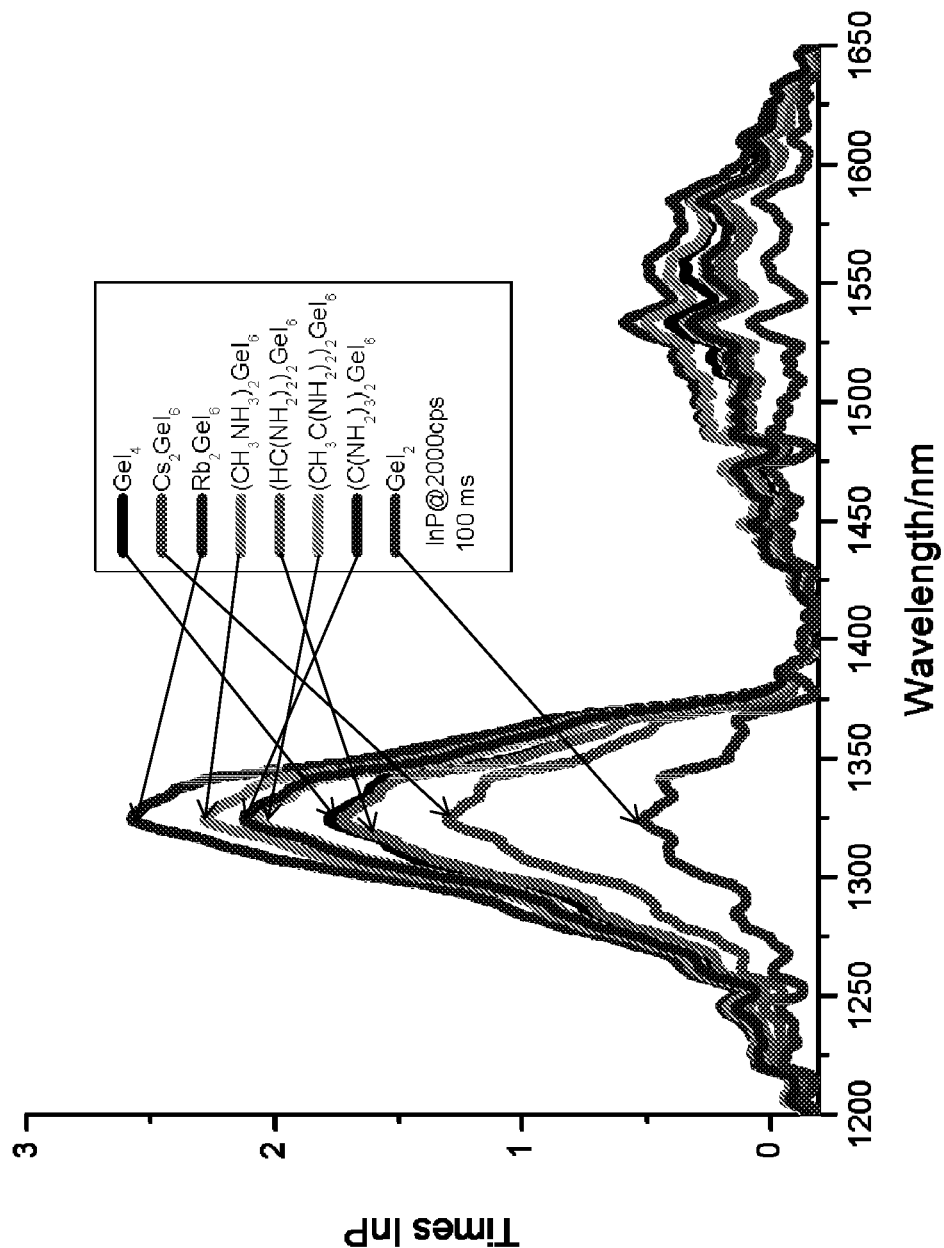
FIG. 20 shows PL emission vs. wavelength spectra for germanium iodide phases.

FIG. 20 shows PL emission vs. wavelength for germanium iodide phases.

Sample Synthetic Process 8:

An alkali metal iodide or an organic iodide salt (1 or 2 equivalents) and $GeI_4$ (1 equivalent) were ground finely at room temperature. The resulting solids were then tested for photoluminescence.

Example 6

This Example provides some illustrative examples of Type V materials and processes for their synthesis. The Type V materials of this example include those comprising two phases, designated categories (G), (H) and (I) in the description that follows.

In this family of materials are incorporated all possible combinations of the materials described as Types I-IV. It is possible to mix i) the halide, X, ii) the octahedrally coordinated metal, M, iii) the cation, A, and iv) it is possible to add another phase to alloy or dope the material (as described in type I), to prepare materials of the general formula $(AMX_3)_{1-x}(M'O_z)_x$, $(AMX_3)_{1-x}(AM'F_6)_x$, (alloying) and $(AM_{1-z}X_{3-z})(M'X_z)$ doping. A denotes any cation, M=Ge, Sn or Pb, M' any element described in type I and X is any halide, as described in Type I-IV materials.

Type V materials of category (G) have the formula $ASnIX_2xMO_z$: where M=an element described above as a Type I material. Specific examples include: (υ) $(AMX_3)_{1-x}(M'O_z)_x$, where A denotes any cation described above, M=Ge, Sn or Pb, M' any element described above as a Type I material, and X is any halide; and (φ) $(AMX_3)_{1-x}(AM'F_6)_x$, where A denotes any cation described above, M=Ge, Sn or Pb, M' any element described above as a Type I material, and X is any halide.

Figure 21:
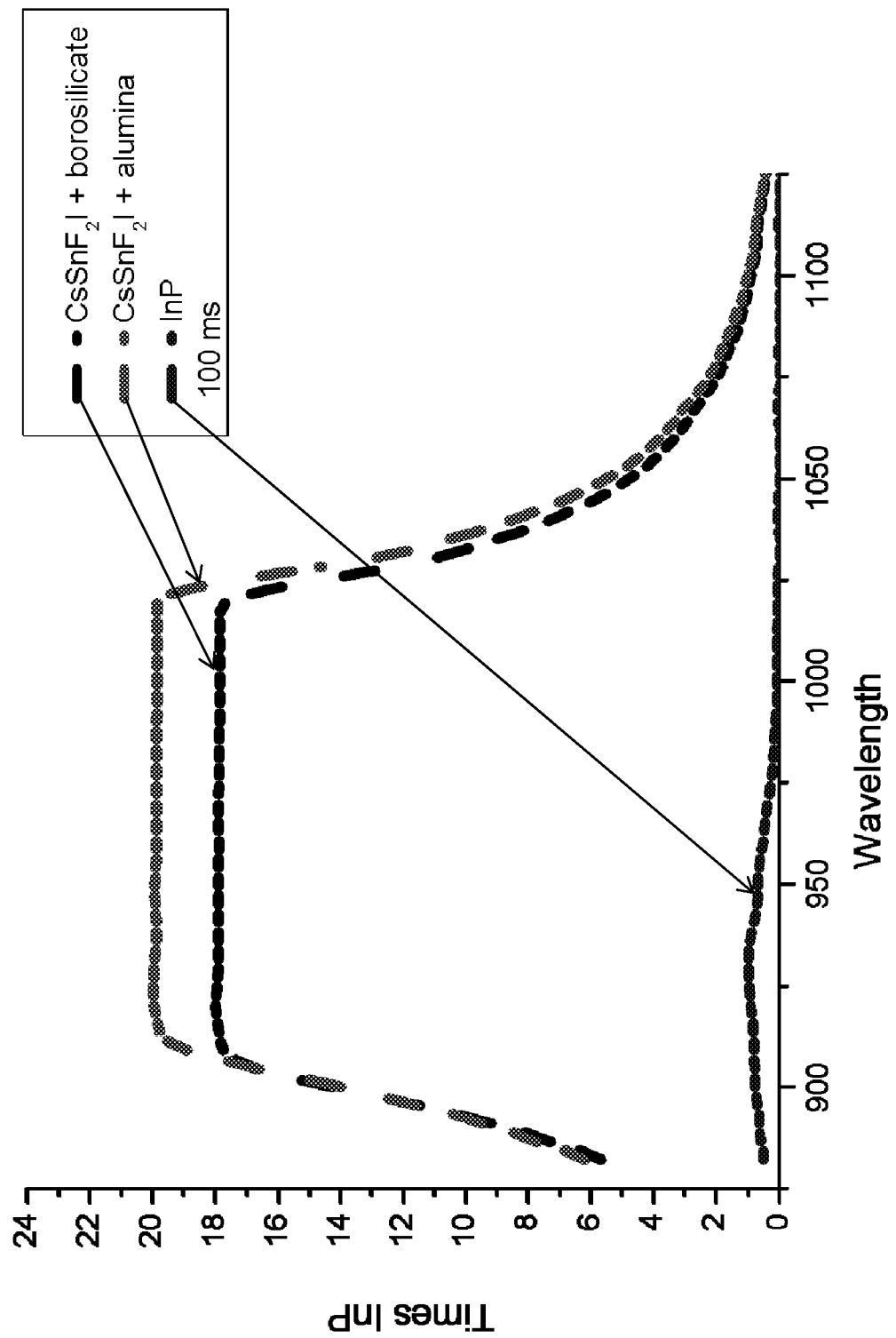
FIG. 21 shows PL emission vs. wavelength spectra for $CsSnF_2I+$ borosilicate and $CsSnF_2I+$ alumina.

FIG. 21 shows PL emission vs. wavelength for $CsSnF_2I$+ borosilicate and $CsSnF_2I$+ alumina.

Sample Synthetic Process 9:

A pyrex ampule or an α-alumina crucible placed inside a pyrex crucible was loaded with CsI (1 equivalent) and $SnF_2$ (1 equivalent). The ampule was sealed under a $10^{-4}$ mbar vacuum and heated up to 350° C. and cooled. The resulting solids were tested for photoluminescence.

Sample Synthetic Process 10:

$CH_3NH_3I$ or $HC(NH_2)_2I$ (1 equivalent), $SnI_2$ or $PbI_2$ or mixtures of them (1 equivalent), where X is a group 17 element, and a variable amount of $CH_3NH_{3z}M'F_6$ or $HC(NH_2)_{2z}M'F_6$ were ground finely at room temperature. The resulting solids were tested for photoluminescence, or first were annealed at elevated temperatures and cooled and then tested for photoluminescence.

Type V materials of category (H) have the formula $AM_{1-x}M'_xX_3$: where M, M'=Ge, Sn, or Pb. Mixing of the metals leads to a shift in the emission wavelength. Specific examples include: (χ) $(AMX_3)_{1-x}(A'M'X'_3)_x$, where A denotes any cation described above, M=M'=Ge, Sn or Pb, and X is any halide.

Figure 22:
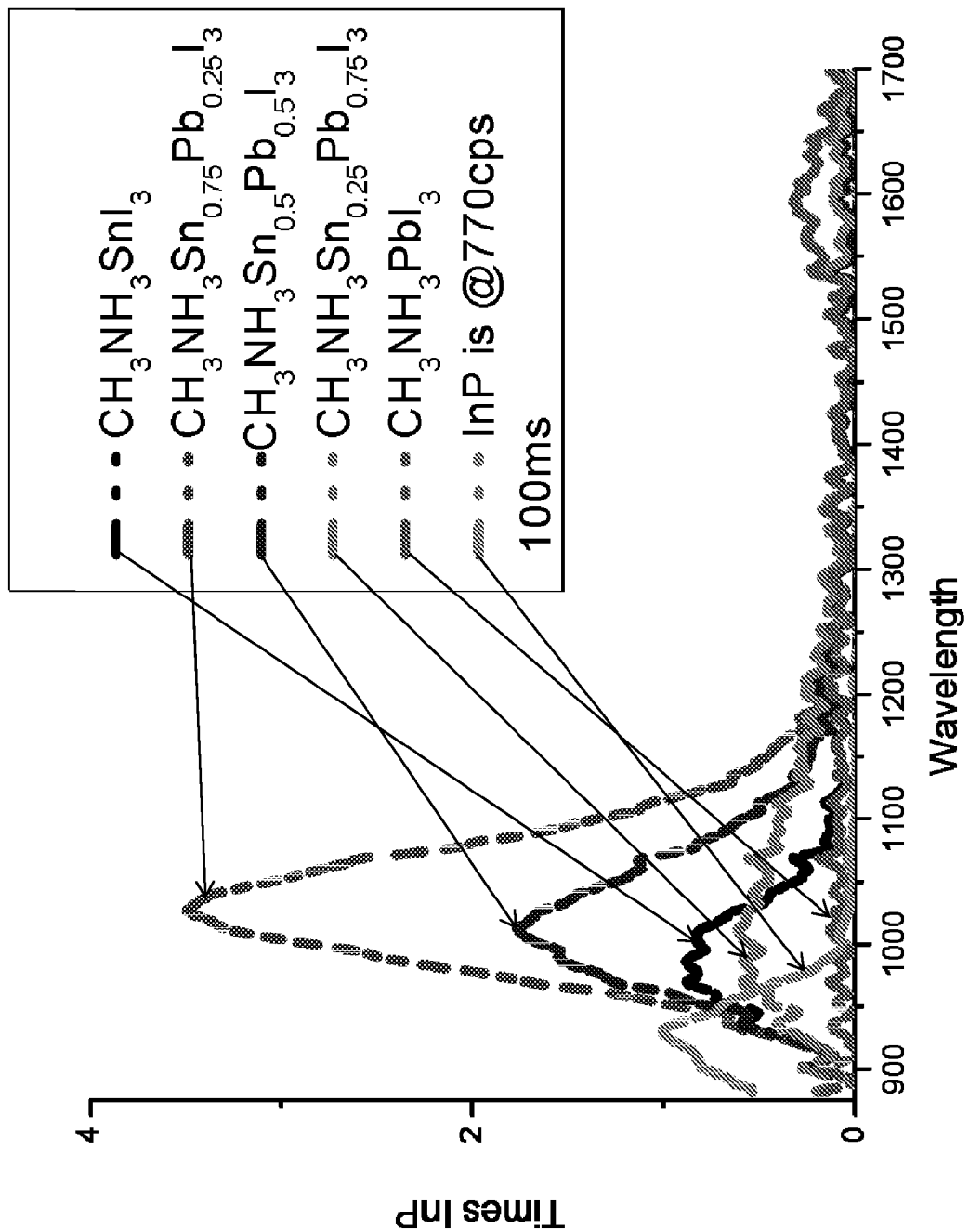
FIG. 22 shows PL emission vs. wavelength spectra for $CH_3NH_3Sn_{1-x}Pb_xI_3$ for different values of x.

FIG. 22 shows PL emission vs. wavelength for $CH_3NH_3Sn_{1-x}Pb_xI_3$ for different values of x.

Sample Synthetic Process 11:

$CH_3NH_3I$ or $HC(NH_2)_2I$ (1 equivalent), $SnI_2$ or $PbI_2$ or mixtures of them (1 equivalent), where X is a Group 17 element, were ground finely at room temperature. The resulting solids were annealed at an elevated temperature and tested for photoluminescence.

Type V materials of category (I) have the formula $(AM_{1-z}X_{3-z})(M'X_z)$: where A is any cation discussed above, M=Ge, Sn, or Pb, M'=a transition metal and X=any halide.

Figure 23:
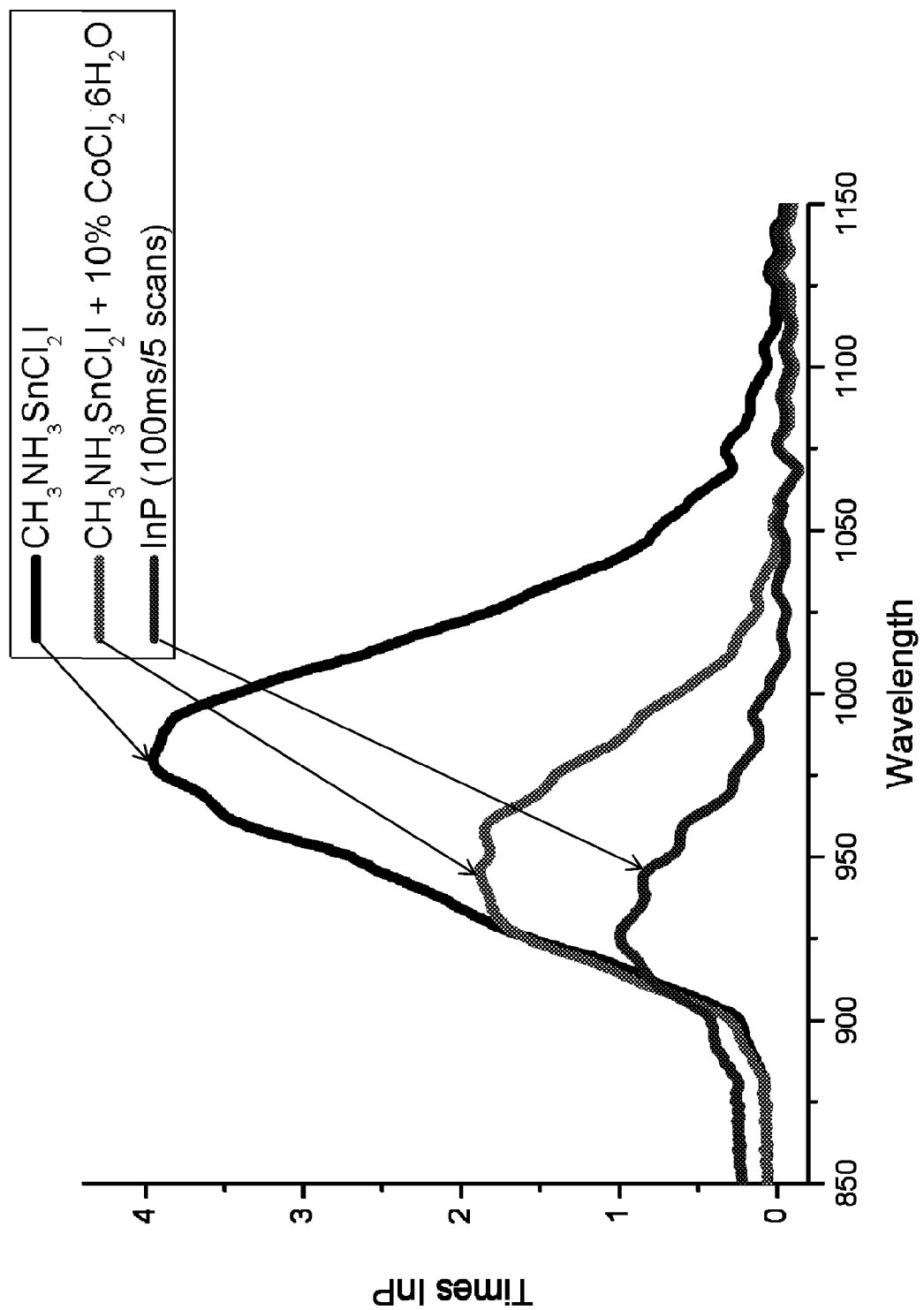
FIG. 23 shows PL emission vs. wavelength spectra for $CH_3NH_3SnCl_2I$, $CH_3NH_3SnCl_2I+10\%$ mol. $CoCl_2\text{-}6H_2O$, and indium phosphide (InP).

FIG. 23 shows PL emission vs. wavelength for $CH_3NH_3SnCl_2I$ and $CH_3NH_3Sn_{0.9}CO_{0.1}Cl_2I$.

Sample Synthetic Process 12:

An alkali metal or an organic iodide salt (1 equivalent), $SnX_2$ or $PbX_2$ and a transition metal halide, where X is a Group 17 element, in a ratio that the total metal content is 1 equivalent, were ground finely at room temperature. The resulting solids were annealed at elevated temperatures and cooled and then tested for photoluminescence.

Unless otherwise specified, the x (or z) values provided in the chemical formulas herein are 0.01<x (or z)<0.99.

Example 7

This Example illustrates methods of making a DSC comprising $CsSnBr_3$ and $CsSnI_2Br$ as HTMs.

Materials and Methods.

Preparation of $CsSnBr_3$ and Other A/M/X Compounds.

Pure $CsSnBr_3$ is prepared by reaching a stoichiometric mixture of CsBr and $SnBr_2$ in an evacuated pyrex or fused silica tube at an elevated temperature for 1 h, followed by quenching or cooling for 1-3 h to room temperature (~23° C.) (RT). The reaction of the stoichiometric mixture of CsBr and $SnBr_2$ is carried out at a temperature in the range of 400°-700° C. The $CsSnI_2Br$ compound (i.e., with Br doping) and the compound doped with $SnF_2$ are made using a procedure analogous to that for F doping and $SnF_2$ doping described in Example 1.

$TiO_2$ Electrode Preparation.

The $TiO_2$ electrode was prepared using the method described in Example 1.

DSC Assembly.

The DSC is assembled according to the process described in Example 1. The structure of the solar cell is the same as that shown in FIG. 1.

JV Characteristics.

The JV characteristics of the solar cell are measured according to the techniques described in Example 1.

TABLE 12

J-V characteristics of the DSCs comprising HTMs of $CsSnI_2Br$, $CsSnBr_3$ and each of these doped with 5% $SnF_2$ using an F-etched $TiO_2$ photoanode under irradiation of 100 mWcm$^{-2}$ simulated AM 1.5 sunlight.

| | | JV characteristics | | | |
|---|---|---|---|---|---|
| | Area (cm$^2$) | $V_{OC}$ (V) | $J_{SC}$ (mA/cm$^2$) | FF (%) | η (%) |
| $CsSnBr_3$ | 0.298 | 0.705 | 6.68 | 62.4 | 2.94 |
| $CsSnI_2Br$ | 0.239 | 0.700 | 17.0 | 68.3 | 8.12 |
| $CsSnBr_3$ + 5% $SnF_2$ | 0.279 | 0.705 | 17.96 | 63.4 | 8.03 |
| $CsSnI_2Br$ + 5% $SnF_2$ | 0.249 | 0.659 | 12.5 | 69.8 | 5.74 |

As shown in the table above the $CsSnBr_{(3-x)}I_x$ materials showed improved $V_{oc}$ and $J_{sc}$ compared to the $CsSnI_3$ system.

Figure 25:
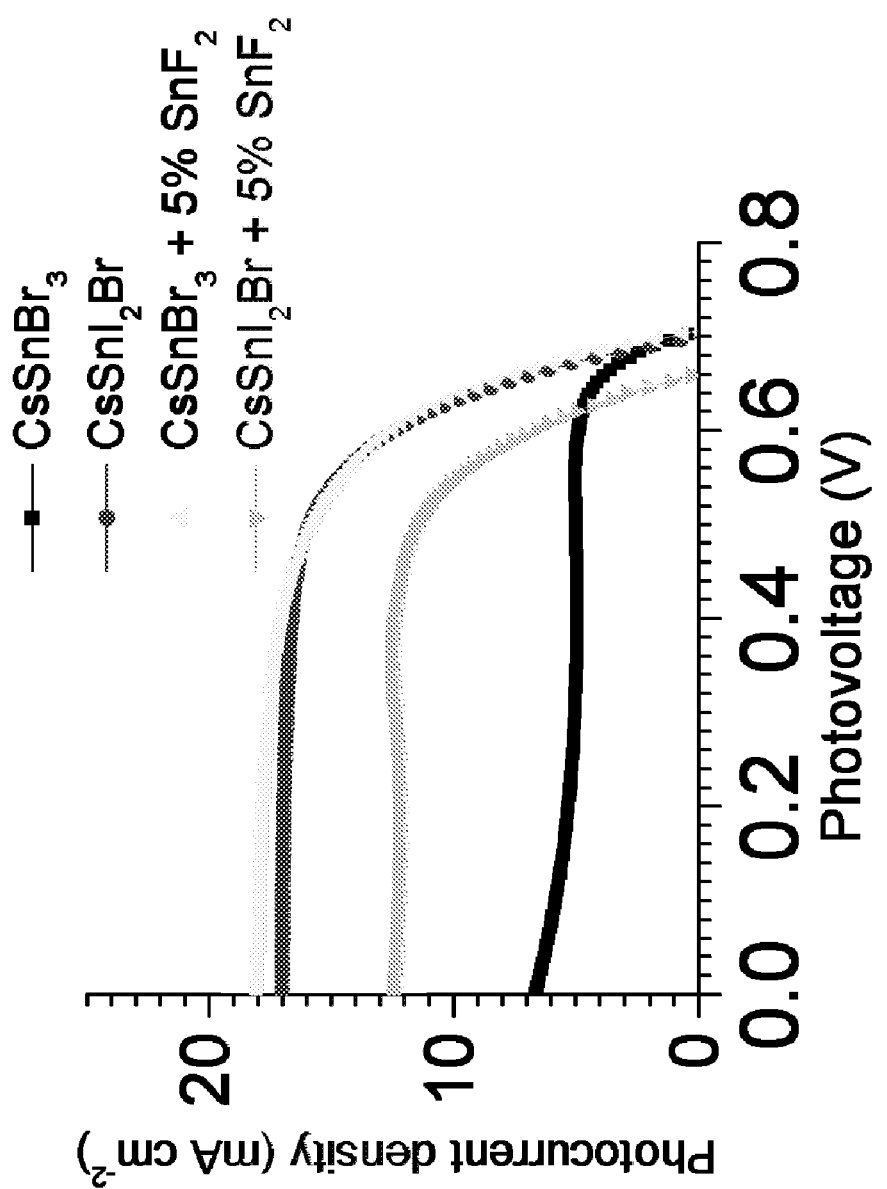
FIG. 25 shows the photocurrent density-voltage (J-V) characteristics of the solar cell devices of Example 7 under irradiation of 100 mWcm$^{-2}$ simulated AM 1.5 sunlight. These solar cells incorporated $CsSnI_3$, $CsSnBr_3$ and $CsSnI_2Br$, as well $CsSnBr_3$ doped with $SnF_2$ and $CsSnI_2Br$ doped with $SnF_2$ as an HTL.

FIG. 25 shows the photocurrent density-voltage (J-V) characteristics of the solar cell devices under irradiation of 100 mWcm$^{-2}$ simulated AM 1.5 sunlight.

Example 8

This Example illustrates the fabrication of pn-junction type solar cells that use A/M/X compounds as hole transport materials, but do not include a photosensitive dye.

FIG. 26 provides a schematic diagram of the solar cell. As shown in panel (D) of FIG. 26, the cell includes a back electrode 2402 comprising a transparent conducting oxide (e.g., FTO), a front electrode comprising and electrically conducting film (e.g., Pt) 2404 disposed on a transparent conducting oxide 2406. Disposed between and electrical communication with electrodes 2402 and 2404/2406 are a layer comprising an n-type $TiO_2$ nanoparticle film 2408 and a layer comprising a A/M/X compound 2410, either $CsSnI_3$ or $CsSnI_{(3-x)}F_x$.

Figure 27:
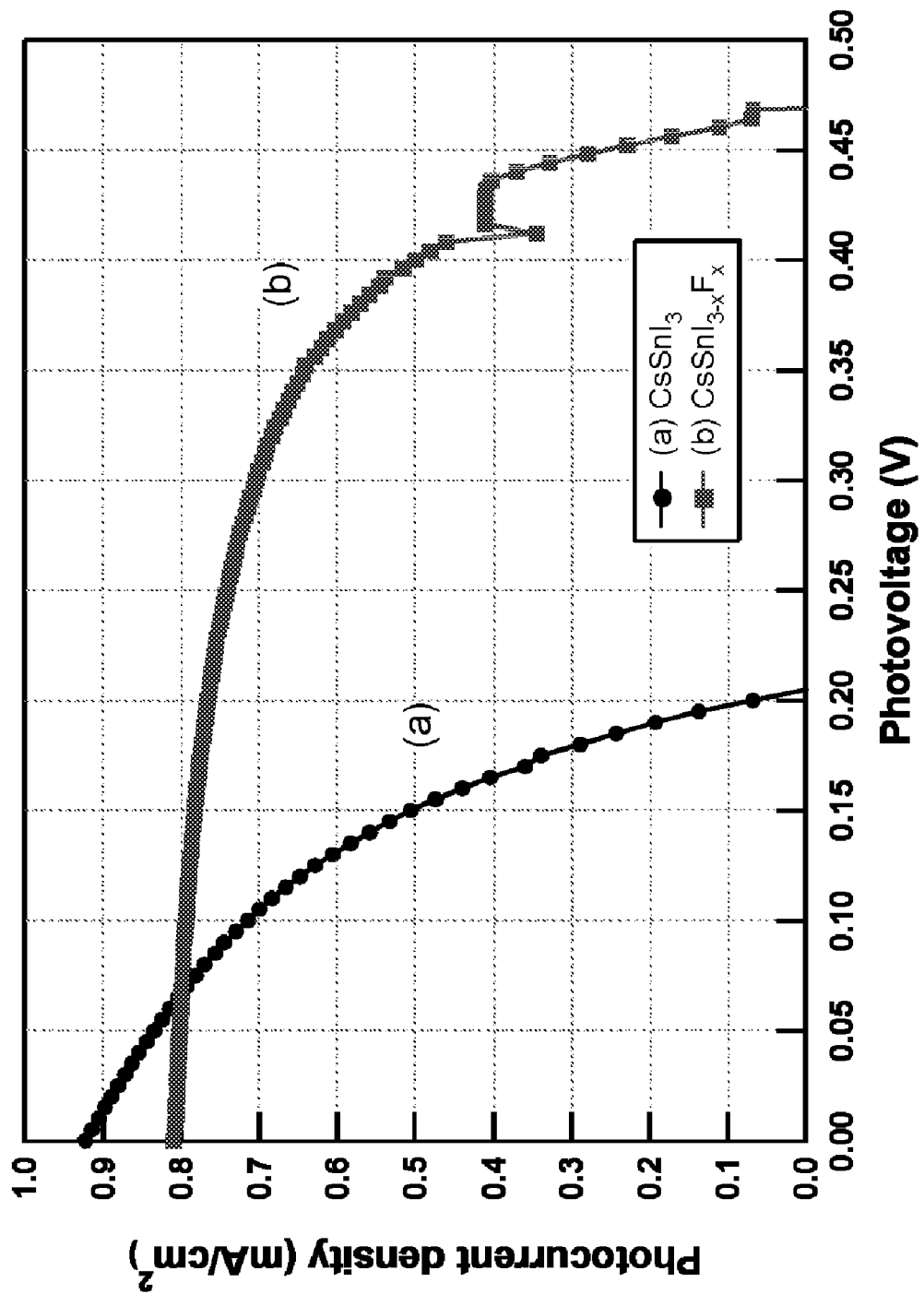
FIG. 27 is a graph of the J-V characteristics of the pn-junction cells of Example 8.

The pn-junction cells were fabricated as follows. The A/M/X compounds (synthesized as described previously) were dispersed in dimethylformamide (DMF) and dropped on the n-type doped $TiO_2$ nanoparticle film (FIG. 26, panels (i) and (ii)). After being drop coated, the films were heated at 150~200° C. until the A/M/X compounds turned black (panel (iii)). And then, the active sides of the resulting film and platinized electrode were mechanically contacted and sealed by Amosil 4 sealant (panel (iv)). The detailed photovoltaic properties (measured as described above) are given in Table 13 and the J-V characteristics are shown in FIG. 27.

TABLE 13

| | $TiO_2$ | | JV characteristics | | | |
|---|---|---|---|---|---|---|
| | Area (cm$^2$) | Thickness (μm) | $V_{OC}$ (V) | $J_{sc}$ (mA/cm$^2$) | FF (%) | EFF (%) |
| (a) $CsSnI_3$ | 0.306 | 12.1 | 0.205 | 0.923 | 41.5 | 0.078 |
| (b) $CsSnI_{3-x}F_x$ | 0.282 | 12.3 | 0.467 | 0.809 | 59.3 | 0.224 |

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A solid state photovoltaic cell comprising:
   (a) a first electrode comprising an electrically conductive material;
   (b) a second electrode comprising an electrically conductive material;
   (c) a porous photoactive material disposed between, and in electrical communication with the first and second electrodes; and
   (d) a hole transporting material comprising an A/M/X compound, wherein the hole transporting material is disposed between the first and second electrodes and is configured to facilitate the transport of holes generated in the photoactive material to one of the first and second electrodes and further wherein the hole transporting material takes the form of a continuous conformal coating that overlies the porous film and also homogeneously infiltrates the pores within the porous film;
   wherein an A/M/X compound is a compound comprising one or more A moieties, one or more M atoms and on or more X atoms, where the A moieties are selected from elements from Group 1 of the periodic table, the M atoms are selected from elements from at least one of Groups 3, 4, 5, 13, 14 or 15 of the periodic table, and the X atoms are selected from elements from Group 17 of the periodic table; and
   further wherein the solid state photovoltaic cell does not comprise a liquid electrolyte and the solid state photovoltaic cell also does not comprise a conducting polymer hole transport material.

2. The photovoltaic cell of claim 1, wherein the photoactive material comprises a porous film of semiconductor oxide having a photosensitizing dye adsorbed thereon.

3. The photovoltaic cell of claim 1, wherein the hole transporting material comprises a p-type semiconducting A/M/X compound and the photoactive material comprises an n-type semiconductor; and further wherein the photoactive material is in contact with the hole transporting material at an interface between the two layers and a pn-junction is formed at said interface.

4. The photovoltaic cell of claim 1, wherein the photoactive material is a photoactive organic polymer.

5. The photovoltaic cell of claim 1, wherein the A/M/X compound has a formula $AMX_3$, where A is a Group I element, M is a Group 14 element and X is a Group 17 element.

6. The photovoltaic cell of claim 1, wherein the A/M/X compound is $CsSnI_3$ doped with a metal halide.

7. The photovoltaic cell of claim 1, wherein the A/M/X compound is $CsSnBr_3$ doped with a metal halide.

8. The photovoltaic cell of claim 1, wherein the A/M/X compound has a formula selected from $AMX_3$, $A_2MX_4$, $AM_2X_5$, $A_2MX_6$ or $AMX_5$, where A is a Group 1 element, M is a Group 14 element and X is a Group 17 element.

9. The photovoltaic cell of claim 1, wherein the A/M/X compound has a formula $AMX_3$, where A is an organic cation, M is a Group 14 element and X is a Group 17 element.

10. The photovoltaic cell of claim 1, wherein the A/M/X compound has a formula selected from $AMX_3$, $A_2MX_4$, $AM_2X_5$, $A_2MX_6$ or $AMX_5$, where A is an organic cation, M is a Group 14 element and X is a Group 17 element.

11. The photovoltaic cell of claim 10, wherein the A/M/X compound is doped with a dopant selected from main group elements, transition metal elements, lanthanide elements, actinide elements or compounds comprising one of more of said elements.

12. The photovoltaic cell of claim 1, wherein the A/M/X compound is a compound comprising one or more A moieties, one or more M atoms and one or more X atoms, where the A moieties are selected from elements from Group 1 of the periodic table, the M atoms are selected from elements from at least one of Groups 3, 4, 5, 13, 14 or 15 of the periodic table, and the X atoms are selected from elements from Group 17 of the periodic table.

13. A photovoltaic cell comprising:
   (a) a first electrode comprising an electrically conductive material;
   (b) a second electrode comprising an electrically conductive material;
   (c) a photoactive material disposed between, and in electrical communication with, the first and second electrodes; and
   (d) a hole transporting material comprising an A/M/X compound, wherein the hole transporting material is disposed between the first and second electrodes and is configured to facilitate the transport of holes generated in the photoactive material to one of the first and second electrodes;
   wherein an A/M/X compound is a compound comprising an A moiety, an M atom, and one or more X atoms, where A is Cs, M is Sn and X comprises one or more halide elements.

14. The photovoltaic cell of claim 13, wherein the photoactive material is in the form of a porous film and the hole transporting material takes the form of a coating that infiltrates the pores of the porous film.

15. The photovoltaic cell of claim 13, wherein the photoactive material comprises a porous film of semiconductor oxide having a photosensitizing dye adsorbed thereon.

16. The photovoltaic cell of claim 13, wherein the hole transporting material comprises a p-type semiconducting A/M/X compound and the photoactive material comprises an n-type semiconductor, and further wherein the photoactive material is in contact with the hole transporting material at an interface between the two layers and a pn-junction is formed at said interface.

17. The photovoltaic cell of claim 13, wherein the photoactive material is a photoactive organic polymer.

18. A photovoltaic cell comprising:
   (a) a first electrode comprising an electrically conductive material;
   (b) a second electrode comprising an electrically conductive material;
   (c) a photoactive material disposed between, and in electrical communication with, the first and second electrodes; and
   (d) a hole transporting material comprising an A/M/X compound, wherein the hole transporting material is disposed between the first and second electrodes and is configured to facilitate the transport of holes generated in the photoactive material to one of the first and second electrodes;
   wherein an A/M/X compound is a compound comprising one or more A moieties, one or more M atoms and two or more X elements, where the A moieties are selected from organic cations and elements from Group I of the periodic table, the M atoms are selected from elements from at least one of Groups 3, 4, 5, 13, 14 or 15 of the periodic table, and further wherein the A/M/X compound has the formula $AMX_{(3-x)}X'_x$, where X and X' are different halogen atoms and $0.01<x<0.99$.

19. The photovoltaic cell of claim 18, wherein the A/M/X compound is doped with a metal halide, such that the material comprises a first phase comprising $AMX_{(3-x)}X'_x$ and a second phase comprising the metal halide dopant.

20. The photovoltaic cell of claim 18, wherein X is I and X' is F.

21. The photovoltaic cell of claim 20, wherein the A/M/X compound is doped with a metal halide, such that the material comprises a first phase comprising $AMX_{(3-x)}X'_x$ and a second phase comprising the metal halide dopant.

22. The photovoltaic cell of claim 21, comprising $CsSnI_{(3-x)}F_x$ doped with $SnF_2$.

23. The photovoltaic cell of claim 18, wherein X is I and X' is Br.

24. The photovoltaic cell of claim 23, wherein the A/M/X compound is doped with a metal halide, such that material comprises a first phase comprising $AMX_{(3-x)}X'_x$ and a second phase comprising the metal halide dopant.

25. The photovoltaic cell of claim 24, comprising $CsSnI_{(3-x)}Br_x$.

26. The photovoltaic cell of claim 25, comprising $CsSnI_{(3-x)}Br_x$ doped with $SnF_2$.

27. The photovoltaic cell of claim 20, comprising $CsSnI_{(3-x)}F_x$.

28. A solid state photovoltaic cell comprising:
   (a) a first electrode comprising an electrically conductive material;
   (b) a second electrode comprising an electrically conductive material;
   (c) a porous photoactive material disposed between, and in electrical communication with, the first and second electrodes, the photoactive material comprising a porous film and a continuous conformal coating comprising an A/M/X compound that overlies the porous film and also homogeneously infiltrates the pores within the porous film, wherein an A/M/X compound is a compound comprising one or more A moieties, one or more M atoms and one or more X atoms, where the A moieties are selected from elements from Group 1 of the period table, the M atoms are selected from elements from at least one of Groups 3, 4, 5, 13, 14 or 15 of the period table, and the X atoms are selected from elements from Group 17 of the periodic table;
   wherein the solid state photovoltaic cell does not comprise a liquid electrolyte and the solid state photovoltaic cell does not comprise a conducting polymer hole transport material.

29. A solid state photovoltaic cell comprising:
   (a) a first electrode comprising an electrically conductive material;
   (b) a second electrode comprising an electrically conductive material;
   (c) a porous photoactive material disposed between, and in electrical communication with, the first and second electrodes, the photoactive material comprising a porous film and a continuous conformal coating comprising an A/M/X compound that overlies the porous film and also homogeneously infiltrates the pores within the porous film, wherein an A/M/X compound is a compound comprising one or more A moieties, one or more M atoms and one or more X atoms, where the A moieties are selected from elements from Group 1 of the periodic table, the M atoms are selected from elements from at least one of Groups 3, 4, 5, 13, 14 or 15 of the periodic table, and the X atoms are selected from elements from Group 17 of the periodic table;
   wherein the solid state photovoltaic cell does not comprise a liquid electrolyte.

30. The photovoltaic cell of claim 29, where A is Cs, M is Sn and X comprises one or more halide elements.

31. The photovoltaic cell of claim 30, comprising $CsSnI_{(3-x)}F_x$, where $0.01<x<0.99$.

32. The photovoltaic cell of claim 29, wherein the A/M/X compound has a formula $AMX_3$, where M is a Group 14 element and X is a Group 17 element.

33. The photovoltaic cell of claim 29, wherein the A/M/X compound is $CsSnI_3$ doped with a metal halide.

34. The photovoltaic cell of claim 29, wherein the A/M/X compound is $CsSnBr_3$ doped with a metal halide.

* * * * *